(12) United States Patent
Talbert et al.

(10) Patent No.: US 10,874,292 B2
(45) Date of Patent: Dec. 29, 2020

(54) SYSTEM AND METHOD FOR PROVIDING A SINGLE USE IMAGING DEVICE FOR MEDICAL APPLICATIONS

(71) Applicant: DePuy Synthes Products, Inc., Raynham, MA (US)

(72) Inventors: Joshua D. Talbert, Salt Lake City, UT (US); Jeremiah D. Henley, Sal Lake City, UT (US); Donald M. Wichern, South Ogden, UT (US); Curtis L. Wichern, Salt Lake City, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/405,860

(22) Filed: May 7, 2019

(65) Prior Publication Data

US 2019/0261838 A1 Aug. 29, 2019

Related U.S. Application Data

(63) Continuation of application No. 14/635,831, filed on Mar. 2, 2015, now Pat. No. 10,413,165, which is a
(Continued)

(51) Int. Cl.
*G06F 21/00* (2013.01)
*A61B 1/04* (2006.01)
(Continued)

(52) U.S. Cl.
CPC ............... *A61B 1/04* (2013.01); *G16H 40/63* (2018.01); *H04L 9/32* (2013.01); *H04N 7/183* (2013.01)

(58) Field of Classification Search
CPC ............................ G06F 19/3406; H04N 7/183
See application file for complete search history.

(56) References Cited

U.S. PATENT DOCUMENTS

| 3,796,220 A | 3/1974 | Bredemeier |
| 3,858,577 A | 1/1975 | Bass et al. |

(Continued)

FOREIGN PATENT DOCUMENTS

| CN | 101273330 A | 9/2008 |
| CN | 102576185 A | 7/2012 |

(Continued)

OTHER PUBLICATIONS https://www4.j-platpat.inpit.go.jp/eng/tokujitsu/tkbs_en/TKBS_EN_GM401_Detailed.action, English Translation of JP 2004-165728.
(Continued)

*Primary Examiner* — Jeffrey C Pwu
*Assistant Examiner* — Helai Salehi
(74) *Attorney, Agent, or Firm* — Terrence J. Edwards; TechLaw Ventures, PLLC

(57) ABSTRACT

A system and methods for providing and reclaiming a single use imaging device for sterile environments is disclosed and described. The system may include a single use high definition camera used for general purpose surgical procedures including, but not limited to: arthroscopic, laparoscopic, gynecologic, and urologic procedures, may comprise an imaging device that is a sterile and designed to ensure single use. The imaging device may have a single imaging sensor, either CCD or CMOS, encased in a housing.

30 Claims, 33 Drawing Sheets

Related U.S. Application Data continuation of application No. 13/072,615, filed on Mar. 25, 2011, now Pat. No. 8,972,714.

(60) Provisional application No. 61/317,630, filed on Mar. 25, 2010.

(51) Int. Cl.
  *G16H 40/63* (2018.01)
  *H04N 7/18* (2006.01)
  *H04L 9/32* (2006.01)

(56) References Cited

U.S. PATENT DOCUMENTS

| | | |
|---|---|---|
| 4,011,403 A | 3/1977 | Epstein et al. |
| 4,153,356 A | 5/1979 | Hama |
| 4,350,150 A | 9/1982 | Kubota et al. |
| 4,429,686 A | 2/1984 | Hosoda |
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkie et al. |
| 4,800,424 A | 1/1989 | Noguchi |
| 4,831,444 A | 5/1989 | Kato |
| 4,888,639 A | 12/1989 | Yabe et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,042,915 A | 8/1991 | Akutsu et al. |
| 5,115,309 A | 5/1992 | Hang |
| 5,168,863 A | 12/1992 | Kurtzer |
| 5,227,662 A | 7/1993 | Ohno et al. |
| 5,237,403 A | 8/1993 | Sugimoto et al. |
| 5,277,172 A | 1/1994 | Sugimoto |
| 5,289,555 A | 2/1994 | Sanso |
| 5,307,804 A | 5/1994 | Bonnet |
| 5,381,784 A | 1/1995 | Adair |
| 5,400,267 A | 3/1995 | Denen et al. |
| 5,489,801 A | 2/1996 | Blish, II |
| 5,494,483 A | 2/1996 | Adair |
| 5,522,006 A | 5/1996 | Takeuchi et al. |
| 5,576,781 A | 11/1996 | Deleeuw |
| 5,589,874 A | 12/1996 | Buchin |
| 5,594,282 A | 1/1997 | Otsuki |
| 5,614,763 A | 3/1997 | Womack |
| 5,757,075 A | 5/1998 | Kitaoka |
| 5,830,121 A | 11/1998 | Enomoto et al. |
| 5,879,289 A | 3/1999 | Yarush et al. |
| 5,896,166 A | 4/1999 | D'Alfonso et al. |
| 5,929,901 A | 7/1999 | Adair et al. |
| 5,966,210 A * | 10/1999 | Rosow ............... A61B 1/00057 356/213 |
| 5,986,693 A | 11/1999 | Adair et al. |
| 6,043,839 A | 3/2000 | Adair et al. |
| 6,059,776 A | 5/2000 | Gatto |
| 6,059,793 A | 6/2000 | Pagedas |
| 6,080,101 A | 6/2000 | Tatsuno et al. |
| 6,092,926 A | 7/2000 | Still et al. |
| 6,211,904 B1 | 4/2001 | Adair et al. |
| 6,266,551 B1 * | 7/2001 | Osadchy ............ A61B 1/00059 600/424 |
| 6,275,255 B1 | 8/2001 | Adair et al. |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,390,972 B1 | 5/2002 | Speier et al. |
| 6,404,048 B2 | 6/2002 | Akram |
| 6,424,369 B1 | 7/2002 | Adair et al. |
| 6,436,032 B1 | 8/2002 | Eto et al. |
| 6,452,626 B1 | 9/2002 | Adair et al. |
| 6,456,326 B2 | 9/2002 | Fossum et al. |
| 6,588,884 B1 | 7/2003 | Furlani et al. |
| 6,720,810 B1 | 4/2004 | New |
| 6,726,620 B2 | 4/2004 | Shibata et al. |
| 6,784,940 B1 | 8/2004 | Takazawa et al. |
| 6,812,949 B1 | 11/2004 | Switzer et al. |
| 6,847,490 B1 | 1/2005 | Nordstrom et al. |
| 6,862,036 B2 | 3/2005 | Adair et al. |
| 6,976,954 B2 | 12/2005 | Takahashi |
| 6,982,740 B2 | 1/2006 | Adair et al. |
| 6,982,742 B2 | 1/2006 | Adair et al. |
| 6,997,871 B2 | 2/2006 | Sonnenschein et al. |
| 7,002,621 B2 | 2/2006 | Adair et al. |
| 7,018,331 B2 | 3/2006 | Chang et al. |
| 7,030,904 B2 | 4/2006 | Adair et al. |
| 7,061,117 B2 | 6/2006 | Yang et al. |
| 7,070,560 B2 | 7/2006 | Takahashi |
| 7,088,398 B1 | 8/2006 | Wolf et al. |
| 7,115,091 B2 | 10/2006 | Root et al. |
| 7,193,519 B2 | 3/2007 | Root et al. |
| 7,227,469 B2 | 6/2007 | Varner et al. |
| 7,230,615 B2 | 6/2007 | Wang et al. |
| 7,258,546 B2 | 8/2007 | Beier et al. |
| 7,274,390 B2 | 9/2007 | Sevat et al. |
| 7,276,785 B2 | 10/2007 | Bauer et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 12/2007 | Couvillon, Jr. |
| 7,317,955 B2 | 1/2008 | McGreevy |
| 7,331,523 B2 | 2/2008 | Meier et al. |
| 7,339,982 B2 | 3/2008 | Wood, Jr. |
| 7,386,084 B2 | 6/2008 | Yin |
| 7,402,811 B2 | 7/2008 | Hatanaka et al. |
| 7,443,296 B2 | 10/2008 | Mezhinsky et al. |
| 7,517,351 B2 | 4/2009 | Culp et al. |
| 7,535,037 B2 | 5/2009 | Lyu |
| 7,542,069 B2 | 6/2009 | Tashiro |
| 7,551,059 B2 | 6/2009 | Farrier |
| 7,568,619 B2 | 8/2009 | Todd et al. |
| 7,578,786 B2 | 8/2009 | Boulais et al. |
| 7,598,686 B2 | 10/2009 | Lys et al. |
| 7,599,439 B2 | 10/2009 | Lavelle et al. |
| 7,768,562 B2 | 8/2010 | Boemler |
| 7,795,650 B2 | 9/2010 | Eminoglu et al. |
| 7,800,192 B2 | 9/2010 | Venezia et al. |
| 7,824,328 B2 | 11/2010 | Gattani et al. |
| 7,868,283 B2 | 1/2011 | Mabuchi |
| 7,871,373 B2 | 1/2011 | Yamada |
| 7,880,662 B2 | 2/2011 | Bogaerts |
| 8,648,932 B2 | 2/2014 | Talbert et al. |
| 8,972,714 B2 | 3/2015 | Talbert et al. |
| 10,413,165 B2 | 9/2019 | Talbert et al. |
| 2001/0041825 A1 | 11/2001 | Shibata et al. |
| 2001/0052930 A1 | 12/2001 | Adair et al. |
| 2002/0006309 A1 | 1/2002 | Batholoma et al. |
| 2002/0017611 A1 | 2/2002 | Tashiro et al. |
| 2002/0067408 A1 | 6/2002 | Adair et al. |
| 2002/0080248 A1 | 6/2002 | Adair et al. |
| 2002/0161460 A1 | 10/2002 | Noghuchi |
| 2002/0163578 A1 | 11/2002 | Adair et al. |
| 2002/0180867 A1 | 12/2002 | Adair et al. |
| 2003/0093805 A1 | 5/2003 | Gin |
| 2003/0129863 A1 | 7/2003 | Alcoe et al. |
| 2003/0187586 A1 | 10/2003 | Katzenmaier et al. |
| 2004/0049215 A1 | 3/2004 | Snow et al. |
| 2004/0078494 A1 | 4/2004 | Lennox et al. |
| 2004/0111012 A1 | 6/2004 | Whitman |
| 2004/0169771 A1 | 9/2004 | Washington et al. |
| 2004/0188302 A1 | 9/2004 | Rogers, Jr. |
| 2004/0249267 A1 | 12/2004 | Gilboa |
| 2005/0071916 A1 | 4/2005 | Rooke et al. |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |

(56) References Cited

U.S. PATENT DOCUMENTS

| | | |
|---|---|---|
| 2005/0261551 A1 | 11/2005 | Couvillon, Jr. |
| 2006/0022234 A1 | 2/2006 | Adair et al. |
| 2006/0221230 A1 | 10/2006 | Dutta et al. |
| 2006/0249765 A1 | 11/2006 | Hsieh |
| 2006/0293563 A1 | 12/2006 | Banik et al. |
| 2006/0293565 A1 | 12/2006 | Uchimura et al. |
| 2007/0030345 A1 | 2/2007 | Amling et al. |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0297190 A1 | 12/2007 | Ng |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0208297 A1 | 8/2008 | Gertner et al. |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0258042 A1 | 10/2008 | Krymski |
| 2008/0268561 A1 | 10/2008 | Banik et al. |
| 2008/0287798 A1 | 11/2008 | Lee et al. |
| 2008/0309810 A1 | 12/2008 | Smith et al. |
| 2008/0312505 A1 | 12/2008 | Schaaf |
| 2008/0316319 A1 | 12/2008 | Nomoto |
| 2009/0015301 A1 | 1/2009 | Marchesini et al. |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0076239 A1 | 3/2009 | Zie et al. |
| 2009/0082630 A1 | 3/2009 | Tulley |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0173974 A1 | 7/2009 | Shah et al. |
| 2009/0184349 A1 | 7/2009 | Dungan |
| 2009/0192390 A1 | 7/2009 | Berguer et al. |
| 2009/0200624 A1 | 8/2009 | Dai et al. |
| 2009/0203966 A1 | 8/2009 | Mizuyoshi |
| 2009/0212397 A1 | 8/2009 | Tuttle |
| 2009/0230287 A1 | 9/2009 | Anderson et al. |
| 2009/0236500 A1 | 9/2009 | Shah et al. |
| 2009/0244363 A1 | 10/2009 | Sugimura et al. |
| 2009/0253967 A1 | 10/2009 | Gill et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0306478 A1 | 12/2009 | Mizuyoshi |
| 2009/0322911 A1 | 12/2009 | Blanquart |
| 2009/0322912 A1 | 12/2009 | Blanquart |
| 2010/0026824 A1 | 2/2010 | Chen |
| 2010/0059802 A1 | 3/2010 | Chen |
| 2010/0118932 A1 | 5/2010 | Luo et al. |
| 2010/0178722 A1 | 7/2010 | de Graff et al. |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0298700 A1 | 11/2010 | Pinot et al. |
| 2010/0302734 A1 | 12/2010 | Beaupre et al. |
| 2011/0028790 A1 | 2/2011 | Farr et al. |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049591 A1 | 3/2011 | Nakatani et al. |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0156235 A1 | 6/2011 | Yuan |
| 2011/0160514 A1 | 6/2011 | Long et al. |
| 2011/0181709 A1 | 7/2011 | Wright et al. |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0238977 A1 | 9/2011 | Talbert et al. |
| 2011/0298169 A1 | 12/2011 | Nguyen et al. |
| 2012/0090876 A1 | 4/2012 | Dower et al. |
| 2014/0012138 A1 | 1/2014 | Talbert et al. |
| 2019/0261838 A1 | 8/2019 | Talbert et al. |

FOREIGN PATENT DOCUMENTS

| | | |
|---|---|---|
| CN | 201080045204.7 | 9/2016 |
| CN | 109905669 A | 6/2019 |
| JP | Hei04-503173 | 6/1992 |
| JP | H05-038324 | 2/1993 |
| JP | 2002-354300 | 12/2002 |
| JP | 2003-126018 A | 5/2003 |
| JP | 2003-272009 A | 9/2003 |
| JP | 2003-325432 | 11/2003 |
| JP | 2004-148124 A | 5/2004 |
| JP | 2003-038424 A1 | 11/2004 |
| JP | 2005152368 A * | 6/2005 |
| JP | 2006-230491 A | 9/2006 |
| JP | 2006-296492 | 11/2006 |
| JP | 2007-050108 A | 3/2007 |
| JP | 2007-175505 A | 7/2007 |
| JP | 2007-537825 | 12/2007 |
| JP | 2008-029521 A | 2/2008 |
| JP | 2008-054732 A | 3/2008 |
| JP | 2008-086777 A | 4/2008 |
| JP | 2008-529631 | 8/2008 |
| JP | 2005-530556 A1 | 2/2009 |
| JP | 2006-296675 A1 | 2/2009 |
| JP | 2009-118883 | 6/2009 |
| JP | 2009-160312 | 7/2009 |
| JP | 2005-152368 | 10/2009 |
| JP | 2009-296492 A | 12/2009 |
| JP | 2010-139976 A | 6/2010 |
| JP | 2009-279326 A1 | 6/2011 |
| JP | 2009-178541 A | 3/2016 |
| JP | 2004-165728 | 9/2016 |
| JP | 2009-513283 A1 | 4/2017 |
| WO | 9413191 | 6/1994 |
| WO | 2004093438 A1 | 10/2004 |
| WO | 2006085087 A2 | 8/2006 |
| WO | 2009135255 A1 | 11/2009 |
| WO | 2009142971 A1 | 11/2009 |
| WO | 2011020068 A1 | 2/2011 |

OTHER PUBLICATIONS https://www4.j-platpat.inpit.go.jp/cgi-bin/tran_web_cgi_ejje?u=http://www4.j-platpat.inpit.go.jp/eng/translation/201603120858051283144001746564655 48D3F45DA68D0C2D232DE3FF6793B9B43, English Translation of JP 2005-530556.

https://www4.j-platpat.inpit.go.jp/eng/tokujitsu/tkbs_en/TKBS_EN_GM301_Detailed.action, English Translation of JP 2006-296675.

https://www4.j-platpat.inpit.go.jp/eng/tokujitsu/tkbs_en/TKBS_EN_GM301_Detailed.action, English Translation of JP 2007-175505.

https://www4.j-platpat.inpit.go.jp/eng/tokujitsu/tkbs_en/TKBS_EN_GM301_Detailed.action, English Translation of JP H05-038324.

https://www4.j-platpat.inpit.go.jp/cgi-bin/tran_web_cgi_ejje?u=http://www4.j-platpat.inpit.go.jp/eng/translation/201603120913587113144097103590569 88D3F45DA68D0C2D232DE3FF6793B9B43, English Translation of JP Hei04-503173.

https://www4.j-platpat.inpit.go.jp/eng/tokujitsu/tkbs_en/TKBS_EN_GM301_Detailed.action, English Translation of JP 2009-178541.

https://www4.j-platpat.inpit.go.jp/cgi-bin/tran_web_cgi_ejje?u=http://www4.j-platpat.inpit.go.jp/eng/translation/20160314235608878316

(56) References Cited

OTHER PUBLICATIONS

6669811134065814249C278E53DF9F1A73EA598603EFD9, English Translation of JP 2009-513283.

* cited by examiner

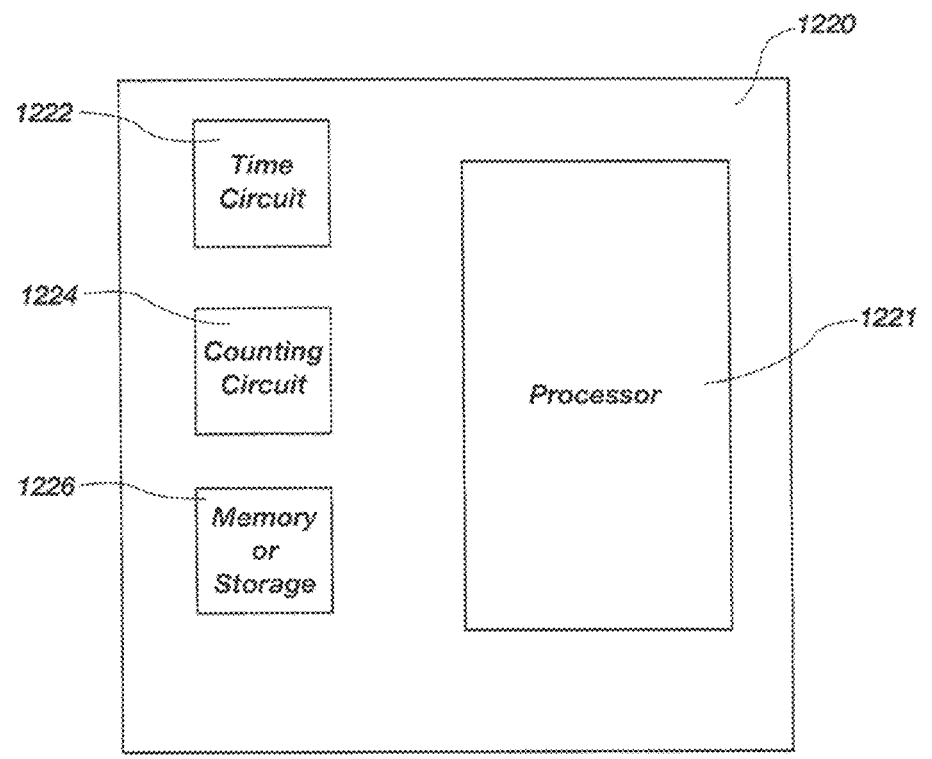
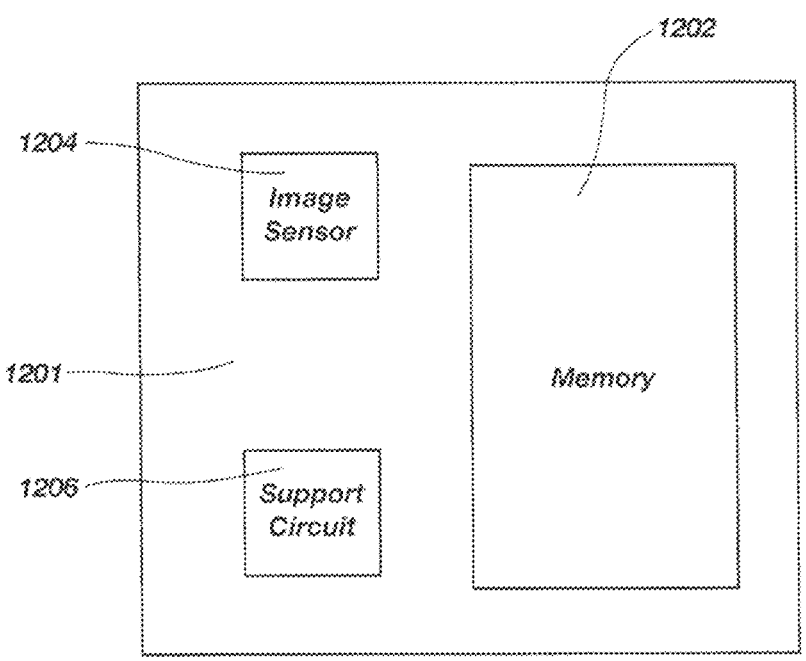
FIG. 12

Receiving an active imaging device

3210

Wherein the imaging device may comprise one or more active electronic components from the group of: field programmable gate array; complex programmable logic device; micro controller; processor; or memory Wherein the imaging device may comprise an image sensor for outputting imaging data authenticating communication between the imaging device and the test fixture by complying with encryption security protocols; built into either or both of the imaging device and the test fixture

Receiving an imaging device that may comprise memory having a control value therein and an image sensor for outputting imaging data

3310 setting a control value in said imaging device memory to allow the imaging device to operate during a medical procedure

3320 sterilizing said imaging device

SYSTEM AND METHOD FOR PROVIDING A SINGLE USE IMAGING DEVICE FOR MEDICAL APPLICATIONS

CROSS-REFERENCE TO RELATED APPLICATIONS

This application is a continuation of U.S. patent application Ser. No. 14/635,831, filed Mar. 2, 2015, which is a continuation of U.S. patent application Ser. No. 13/072,615 filed Mar. 25, 2011 (U.S. Pat. No. 8,972,714), and claims the benefit of U.S. Provisional Application No. 61/317,630, filed on Mar. 25, 2010, which are hereby incorporated herein by reference in their entirety, including but not limited to those portions that specifically appear hereinafter, the incorporation by reference being made with the following exception: In the event that any portion of the above-referenced applications are inconsistent with this application, this application supercedes said above-referenced applications.

STATEMENT REGARDING FEDERALLY SPONSORED RESEARCH OR DEVELOPMENT

Not Applicable.

BACKGROUND

The disclosure relates generally to imaging devices used during surgical procedures to visualize a surgical area, and more particularly, but not necessarily entirely, to a system and methods for providing and reclaiming single use imaging devices primarily for sanitized environments.

Endoscopic surgery is experiencing rapid growth in the medical field. Endoscopy is a minimally invasive surgical procedure that is used to analyze the interior of a body cavity or interior surfaces of an organ by inserting a tubular member into the body cavity through a minor or minimal incision. A conventional endoscope is generally an instrument with a light source and an image sensor or device for visualizing the interior of a body cavity. A wide range of applications have been developed for the general field of endoscopes including, but not necessarily limited to: arthroscope, angioscope, bronchoscope, choledochoscope, colonoscope, cytoscope, duodenoscope, entero scope, esophago-gastro-duodenoscope (gastroscope), laparoscope, laryngoscope, nasopharyngo-neproscope, sigmoidoscope, thoraco scope, and utererscope (hereinafter referred to generally as "endoscope"). The advantages of endoscopy include smaller surgical incisions and less soft tissue damage. As a result, there is significantly less discomfort and pain for the patient as well as a decrease in recovery time.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope. As part of forming an image of the surgical site, the endoscope includes a light source and an image sensor. Endoscopes may also incorporate more than one tubular member for observation or operation within the body, such as a working channel for passing diagnostic, monitoring, treatment, or surgical tools through the endoscope. Endoscopes include glass lenses and an adjustable ocular or eye piece, a lateral connection for a light conductor, an adaptor that allows focusing, and a camera head. This configuration is also called a video endoscope.

Additionally, imaging devices are subject to governmental regulations, for example the FDA in the United States, to protect patients and surgeons from potential infections. These devices may be made and processed in accordance and consistent with international and national regulations for medical environments. The disclosure is directed to a system and method for serializing a medical device, specifically an imaging device such as a camera head.

It is axiomatic that strict sterilization of the operating room and surgical equipment is required during any surgery. The strict hygiene and sterilization conditions required in a "surgical theater," i.e., operating or treatment room, necessitate the highest possible sterility of all medical devices and equipment. Part of that sterilization process is the need to sterilize anything that comes in contact with the patient or penetrates the sterile field, including the endoscope and its attachments and components. It will be appreciated that the sterile field may be considered a specified area, such as within a tray or on a sterile towel, that is considered free of microorganisms; or the sterile field may be considered an area immediately around a patient that has been prepared for a surgical procedure. The sterile field may include the scrubbed team members, who are properly attired, and all furniture and fixtures in the area.

In recent years there has been a trend of providing a single use endoscope and components as a packaged, sterilized product, similar to a package containing a surgical implant, such as a knee or hip implant. In terms of endoscopy, instead of using endoscopes that have been reconditioned for each new surgery through traditional sterilization procedures, it means using a single use endoscope and components that are delivered to the hospital in a sterilized package. Due to this trend, it has become increasingly difficult to ensure that each endoscope and its components are properly cared for, used and sterilized for single use and not simply re-sterilized using traditional sterilization procedures.

Traditional drawbacks or problems of video endoscopes include a lack of image quality, the need for sterilization and high manufacturing cost as well as high processing cost. To address these and potentially other problems, the disclosure utilizes unique imaging devices or sensors in addition to a unique method, system and process for providing and reclaiming single use imaging devices.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein.

SUMMARY OF THE DISCLOSURE

An embodiment may comprise a single use camera used for general purpose surgical procedures including, but not limited to: arthroscopic, laparoscopic, gynecologic, and urologic. An embodiment may comprise an imaging device that is a sterile and designed to ensure single use. An embodiment may be an imaging device that comprises a single imaging sensor, either CCD (charge coupled device) or CMOS (complementary metal oxide semiconductor), encased in a molded plastic housing. It will be appreciated that the housing may be made from metal, carbon fiber or other suitable materials usable as an imaging device housing. The imaging device may further comprise the means to be attached to an optical coupling device, using C-Mount and CS-Mount threads or another proprietary or unique connection method. It is within the disclosure to include integrated optical systems, such that no specific coupling means is required. The imaging device may further comprise a cable or wireless method to transmit data to and from a camera control unit. An embodiment may further comprise a thermal energy dissipation means such as a heat sink or cooling mechanism. An embodiment may further comprise an electrically isolated imaging device, for example a camera head.

In an embodiment, information will be recorded in the memory of the imaging device each time it is used in a procedure or quality control (QC) checked at the manufacturer. This information may be used to evaluate usage time, expiration date, etc. An embodiment may comprise features to ensure that the imaging device is only used once and that the imaging device is safe for use.

In an embodiment, the imaging device may be fully covered in plastic having a sensor heat sink to ensure the camera head meets cardiac floating (CF) and body floating (BF) ISO standards. It will be appreciated that the imaging device may be fully covered in metal, carbon fiber or other suitable materials usable as an imaging device housing. An embodiment may comprise an imaging device that may be stamped with the current time when plugged into a console in the field after a quality control check has been performed. This time may be used as a baseline for usage. If the imaging device is powered off for a predetermined period of time, which may be equivalent to a sterilization cycle, then the imaging device will not function. The imaging device may display an onscreen message telling the user that the camera has already been used and will not allow current operation. These features ensure the imaging device will not be used more than one time per sterilization cycle and further ensures that proper sterilization is performed by the manufacturer or other authorized source. This function is to protect the patient and the doctor from an invalid or unsafe use as well as liability of the manufacturer.

In an embodiment an active imaging device may be attached to a control unit. The control unit will check the last sterilization date and ensure that the imaging device is no older than a predetermined safety date. If the imaging device is older than the required date, an onscreen warning will tell the user that the imaging device has expired and is unsafe for use. These features will protect the patient and the doctor from using a non-sterile imaging device.

In an embodiment a security code or some other means of identifying, and validating for use, an imaging device by a control unit may be provided in order to verify that the imaging device is authorized for use. A validating security code or procedure of validation may be distributed to control units from a central database over the internet, by direct transfer from portable storage device such as USB device containing memory, another computer, or other storage device.

An embodiment may comprise methods for processing single use camera heads including quality control checking, functionality checking, sanitization or sterilization, packaging, transporting, use and reclamation, and reading and writing to memory within the imaging device. An embodiment may comprise a network of components, and may further comprise the ability to update the imaging devices.

BRIEF DESCRIPTION OF THE DRAWINGS

The features and advantages of the disclosure will become apparent from a consideration of the subsequent detailed description presented in connection with the accompanying drawings in which:

FIG. 12 is a layout view of an embodiment of an imaging system made in accordance with the teachings and principles of the disclosure;

FIGS. 31-33 illustrate embodiments of a method and system for processing medical electronic imaging devices in accordance with the teachings and principles of the disclosure.

DETAILED DESCRIPTION

Figure 1:
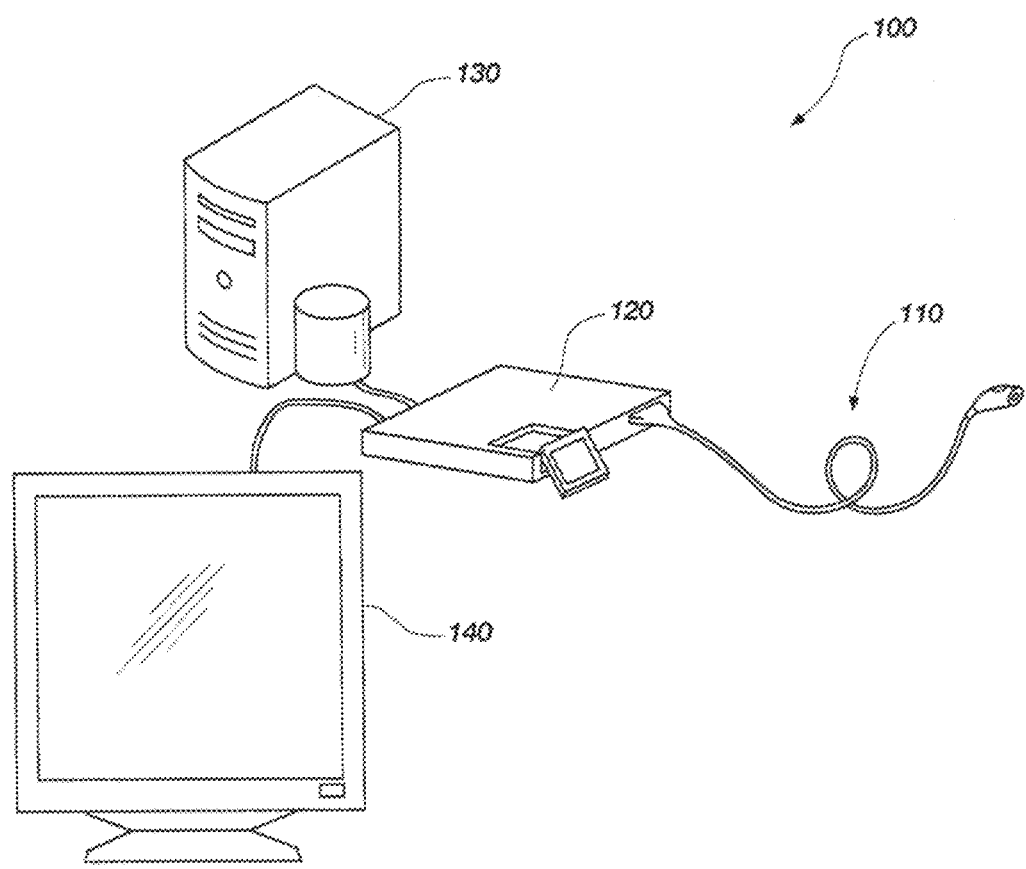
FIG. 1 is an illustration of an embodiment of the features of the disclosure and made in accordance with the teachings and principles of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for providing and reclaiming single use imaging devices are disclosed and described, it is to be understood that this disclosure is not limited to the particular embodiments, configurations, or process steps disclosed herein as such embodiments, configurations, or process steps may vary somewhat. It is also to be understood that the terminology employed herein is used for the purpose of describing particular embodiments only and is not intended to be limiting since the scope of the disclosure will be limited only by the appended claims, if any, and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "active" as used in relation to a device or to electronic communication refers to any device or circuit, driven by hardware or software, that has decision making or logic processing capabilities regarding its operation and/or its condition. Conversely, the term "passive" as used in relation to an imaging device or to electronic communication refers to a hardware device that is written to and read from only, or a device that does not have any memory or other electronic, or physical tracking components and does not include any decision making or logic processing capabilities regarding its operation and/or its condition.

With reference primarily to FIG. 1, an embodiment of the features of the disclosure will be discussed generally. FIG. 1 illustrates a system 100 for providing a digital image using a remote imaging device 110 that may be tethered electronically and physically to a control unit 120. The control unit 120 may be configured to exchange data with imaging device 110 in order to provide single use functionality and safety in a sterile environment, such as an operating room, a doctor's office or dental office. Additionally, the control unit 120 may be electrically connected to a computer 130 or external monitor 140 for increased functionality.

Figure 2:
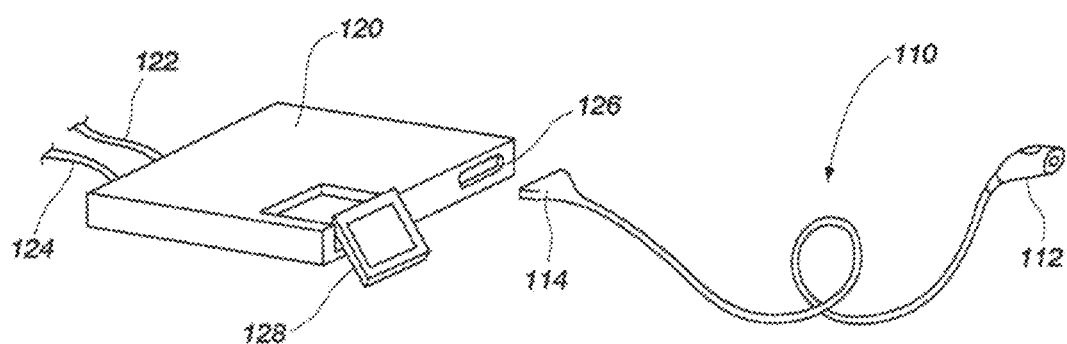
FIG. 2 is an illustration of an embodiment of an imaging system made in accordance with the teachings and principles of the disclosure.

Referring now to FIG. 2 where the imaging system 100 will be discussed in greater detail. As is illustrated in FIG. 2, the imaging device 110 can be connected or disconnected from the control unit 120 by way of an electronic connector 114 on the imaging device 110 that is configured to electronically and physically interact with a corresponding electronic connector 126 on the control unit 120. The ability to disconnect the imaging device 110 from the control unit 120 provides the ability to easily replace a used imaging device 110 for a sterilized, renewed imaging device 110. The imaging device 110 may have a head portion 112 generally positioned remotely from the electronic connector 114, thereby allowing greater mobility of the head portion 112 during use.

Also illustrated in FIG. 2 is an embodiment of the control unit 120 having an electronic connector 126 therein for receiving the corresponding electronic connector 114 of the imaging device 110. The control unit 120 may also have a display 128 for conveying information during a procedure to an operator or user. The display 128 may also comprise interactive functionality allowing an operator to enter commands or change what information is being displayed. Such functionality may be provided by a touch screen system as is commonly known. The control unit may also have video inputs 122 and video outputs 124 for transferring image data to other apparatuses for increased functionality. As illustrated in FIG. 1, common apparatuses may be a computer 130 or an external monitor 140.

Figure 3:
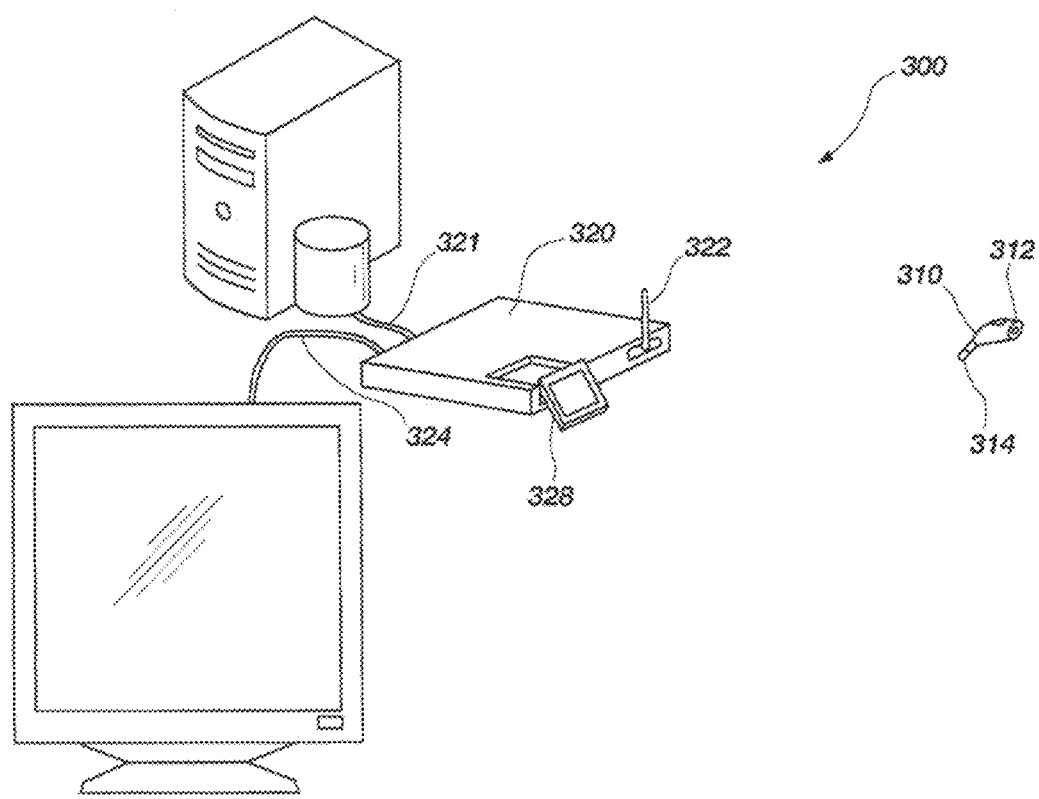
FIG. 3 is an illustration of an imaging system having wireless features made in accordance with the teachings and principles of the disclosure.

Referring now to FIG. 3 an imaging system 300 will be discussed having wireless capability and features. As is illustrated in FIG. 3, the imaging device 310 may communicate with a control unit 320 by way of wireless transmissions such as Wifi, infrared, bluetooth etc. Other forms of wireless non-tethered connectivity may also be used for providing communication between the imaging device 310 and control unit 320, including but not limited to, radio frequency from any available spectrum, infrared of all configurations, ultrasonic, and optical. The imaging device 310 may comprise a head portion 312 that houses an imaging sensor, memory and associated circuitry, which will be discussed in greater detail below. It will be appreciated that in a surgical application, the quality of an image and the ability to adequately view the surgical site is a priority for a surgeon.

The imaging sensor used in the camera head may be a single sensor. Due to the ability to make smaller sized sensors, the single sensor may be located or positioned anywhere along the endoscope. For example, the sensor may be located or positioned proximally with respect to the endoscope, or at the distal end of the endoscope without departing from the spirit or scope of the disclosure. In an embodiment, the imaging sensor may be located on a tip of a device, i.e., in a chip-on-the-tip configuration, such as on the distal end of an endoscope or other component.

It will be appreciated that the imaging sensor may be a combination or plurality of sensors that work together to create a three-dimensional image. The single imaging sensor or the combination or plurality of imaging sensors may be high definition sensors for purposes of creating a high quality image, such that images may be viewed in a high resolution, for example 1920×1080 pixels or any other high definition standard, such as 1280×720 pixels.

The image sensor may be located on a rigid endoscopic member or a flexible endoscopic member. For example, the image sensor may be located on a distal end of an articulating member, such that the sensor may articulate or move for better positioning within a surgical site. In such a case, the camera may be a flexible camera head. It will be appreciated that as the imaging sensor is located closer to the distal end of the endoscope, visualization may be improved. Improved visualization may be due to the amount of light available for the sensor to create an image when the sensor is located distally with respect to the endoscope. Because the location of the sensor may be closer to where the light is being concentrated or focused there may be improved visualization. Thus, in various embodiments, the imaging sensor may be located on a distal end of the endoscope. Further, the imaging sensor may used in a multi-port or single port surgical application. In a single port application, there may be multiple channels through which flexible and rigid instrument delivery tubes are inserted.

The head portion 312 may further comprise a wireless transceiver 314 for communicating with a corresponding wireless transceiver 322 housed in the control unit 320. The ability to separate the head portion 312 from the control unit 320 via wireless transmissions may provide for the easy replacement of used imaging devices for sterilized and renewed imaging devices. In other words, the wireless communication may be enabled by an electronic communication circuit that is a wireless communication transceiver configured to communicate wirelessly with a corresponding transceiver on said control unit using any of the above noted wireless technologies. The wireless functionality also allows for greater mobility of the head portion 312 during use. It will be appreciated that the wireless features and functionality may be incorporated into any of the embodiments disclosed herein or embodiments that fall within the scope of this disclosure.

Also illustrated in FIG. 3 is an embodiment of the control unit 320 having wireless capabilities and features. A transceiver 322 may be provided in or as part of the control unit 320 for receiving and transmitting wireless data to the imaging device 310. The control unit 320 may also have a display 328 for conveying information during a procedure to an operator or user. The display 328 may also comprise interactive functionality allowing an operator to enter commands or change what information is being displayed. Such functionality may be provided by a touch screen system as is commonly known. The control unit 320 may also have video inputs 321 and video outputs 324 for transferring image data to other apparatuses for increased functionality. As illustrated in FIG. 1 common apparatuses may be a computer 130 or an external monitor 140. It is within the scope of this disclosure to include an imaging system comprising both wired and wireless communication capabilities.

Figure 4:
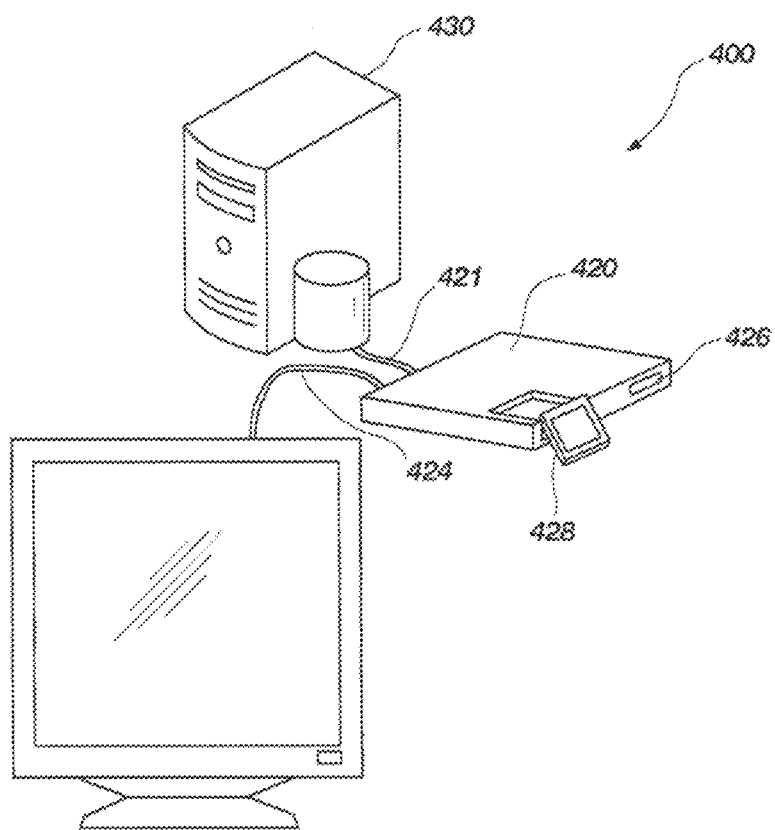
FIG. 4 is an illustration of an embodiment of a control unit disconnected from an imaging device, but illustrated as remaining connected to complementary apparatuses, and made in accordance with the teachings and principles of the disclosure.

Illustrated in FIG. 4 is an embodiment of the control unit 420 disconnected from an imaging device that is illustrated as being connected to complementary apparatuses. A connector 426 may be provided therein for transferring data to and from an imaging device. The ability to separate the imaging device may provide for the easy replacement of used imaging devices with sterilized and renewed imaging devices. The control unit 420 may also have a display 428 for conveying to an operator information during a procedure. The display 428 may also comprise interactive functionality allowing an operator to enter commands or change what information is being displayed. Such functionality may be provided by a touch screen system as is commonly known. The control unit may also have video inputs 421 and video outputs 424 for transferring image data to other apparatuses for increased functionality. Common apparatuses may be a computer 430 or an external monitor 440 there by increasing the technical functionality of the system 400. A computer 430 may be used for storing the digital output from the imaging system or may be used to enhance and provide further adjustment within the system. An external monitor 440 may be used to show real time digital images to aid an operator in the use of the system, or later review and study the recorded digital imagery.

Figure 5:
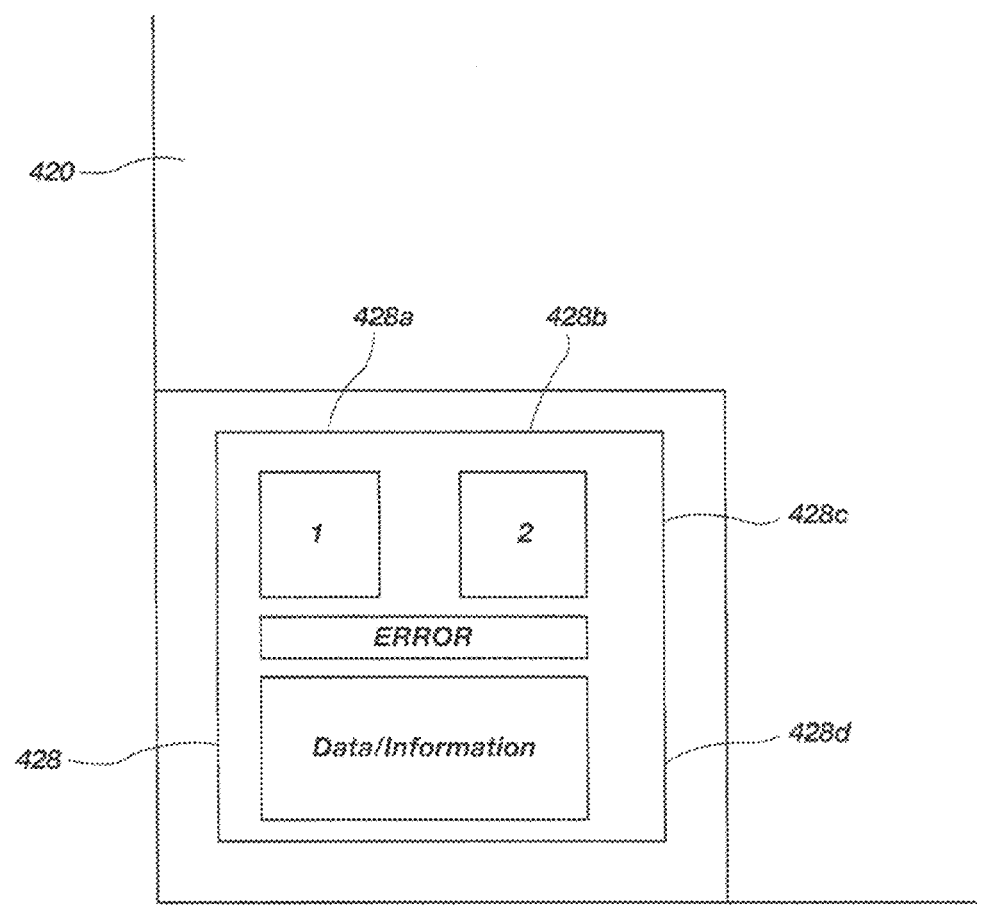
FIG. 5 is an illustration of an embodiment of a control unit display made in accordance with the teachings and principles of the disclosure.

Referring now to FIG. 5 an embodiment of a control unit display 428 that may be part of a control unit 420 will be discussed in greater detail. The display 428 may be a digital display of liquid crystal design (LCD), or the display may be some other technology beside LCD, and may have touch screen functionality and capability for an operator or user to input commands into the system 400. The embodiment discussed herein may have input portions 428*a* and 428*b* whereby an operator or user may input commands into the system 400. The embodiment may further comprise a status portion 428*c* informing a user about the operational status of the components of the system 400. For example, display portion 428*c* may display an error message related to the condition of an attached imaging device 410 if the imaging device 410 has already been used or has been deemed unfit for a procedure. The display 428 may also have a dedicated message portion 428*d* providing instructions and further information to an operator or user. The configuration of the display 428 may change during use to accommodate further functionality. A plurality of displays 428 is contemplated by, and falls within the scope of, this disclosure and may be used alternatively or in conjunction with this embodiment. An embodiment may comprise a key pad or a button pad for control purposes within a control unit.

Figure 6:
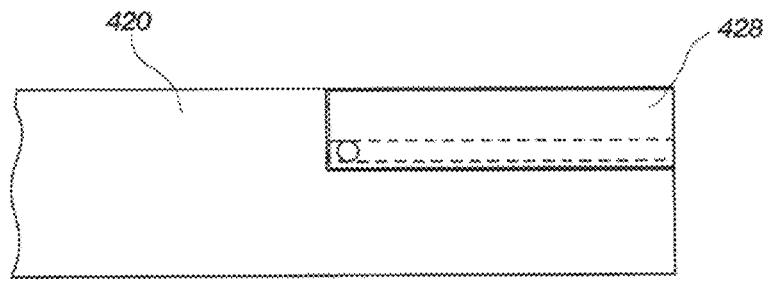
FIG. 6 is an illustration of an embodiment of a retractable display of a control unit in a retracted or closed position and made in accordance with the teachings and principles of the disclosure.
Figure 6A:
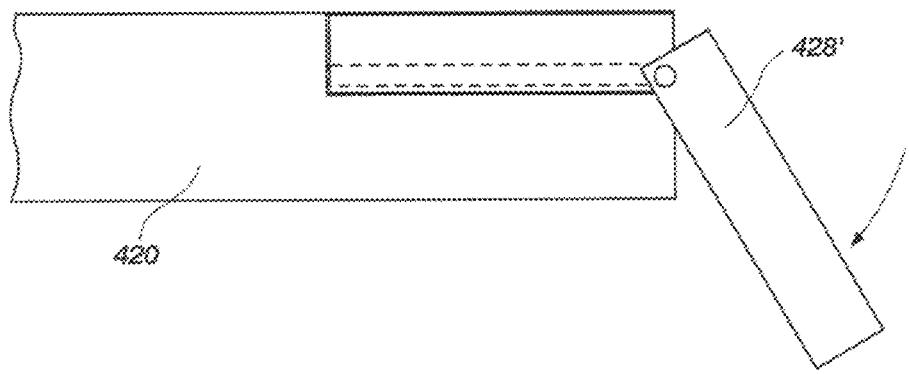
FIG. 6A is an illustration of an embodiment of a retractable display of a control unit in an open position and made in accordance with the teachings and principles of the disclosure.

Illustrated in FIGS. 6 and 6A is an embodiment of a retractable display 428 of a control unit 420. The display 428 may have a first or retracted position within the control unit 420 (illustrated best in FIG. 6) that may be used to protect the display 428 when it is not being used. The display 428' of FIG. 6A illustrates how the display may be deployed into a more user readable position, as it has been extended and rotated outward. As illustrated in FIGS. 6 and 6A, the display may be slid in and out of a passage and rotated about an axis to orient the display 428 in a wide range of positions.

Figure 7:
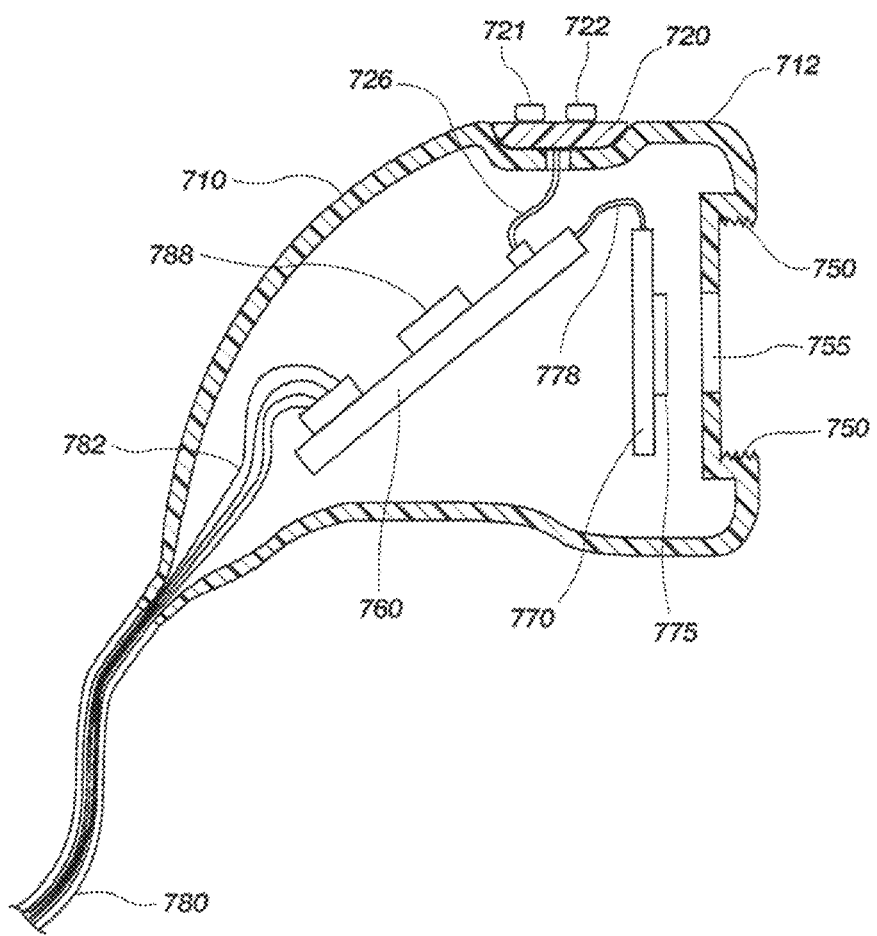
FIG. 7 is a cross-sectional view of an embodiment of an imaging device head made in accordance with the teachings and principles of the disclosure.

Illustrated in FIG. 7 is a cross-sectional view of an embodiment of an imaging device head 712. The imaging device head 712 may comprise a housing 710 made of a suitably rigid material, such as plastic or metal. The housing 710 may be sealed against fluids and gases so as to protect the internal circuitry and provide a suitable surface for sterilization and renewal. The imaging device head 712 may further comprise a user input panel 720 having buttons 721 and 722 for operation of the imaging device head 712. Additional, buttons may be provided and the functionality of the buttons can be customized for a given procedure or a given operator. The control panel 720 may be internally connected to other circuitry of the imaging device head 712 by an electrical connector 726.

As illustrated further in FIG. 7, imaging device head 712 may comprise an optical mount system 750, such as a C-mount system for receiving threaded accessories, for example one inch threaded accessories. A window 755 may also be incorporated into the embodiment for facilitating the transmission of light from an optical accessory to an image sensor 775. The image sensor 775 may be mounted to a supporting printed circuit board or supportive substrate 770. An electronic connector 778 may be incorporated to electronically connect the image sensor 775 to a main circuit or main printed circuit board 760. A main wiring harness 782 may be incorporated into a wired tether 780 thereby electrically connecting the components of the imaging device head 712 to a control unit.

The imaging device head 712 may further comprise a memory 788 or memory circuit allowing the storage of data within the imaging device head 712. It will be appreciated that memory may be any data storage device that is capable of recording (storing) information (data). Data that may be stored or written into memory 788 may include an identifying serial number that uniquely identifies an imaging device. Other data that may be stored or written into memory 788 may include data such as the amount of the time the imaging device has been used, i.e., the hours of operation, or the amount of time the imaging device has been powered on. Data that may be written into memory 788 may include sterilization data or renewal data, representing the working condition of the imaging device. Data that may be stored or written into memory 788 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 788 may be encryption protected so as to avoid tampering or unintended use and foreseeable misuse. It should be noted that a memory 788 may be placed anywhere in the imaging device and not just the imaging device head without departing from the scope of the disclosure. The memory 788 may comprise a permanent or semi-permanent portion allowing varying degrees of data durability.

Figure 8:
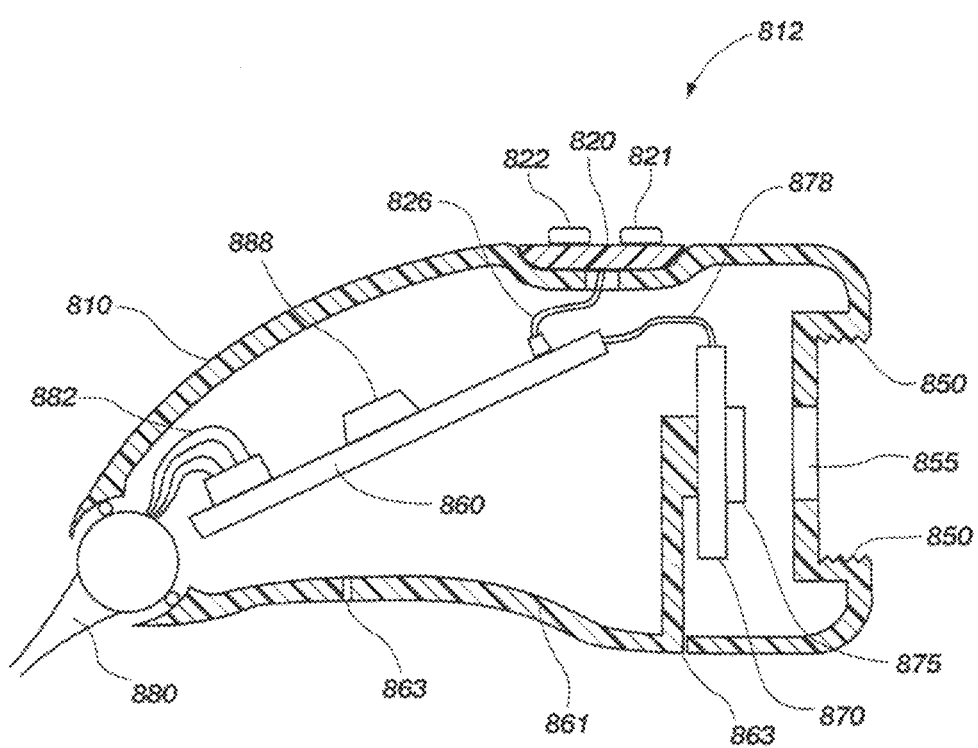
FIG. 8 is a cross-sectional view of an embodiment of an imaging device head made in accordance with the teachings and principles of the disclosure.

Illustrated in FIG. 8 is a cross-sectional view of an embodiment of an imaging device head 812. The imaging device head 812 may comprise a housing 810 made of a suitably rigid material such as plastic or metal. The housing 810 may be sealed against fluids and gases so as to protect the internal circuitry and provide a suitable surface for sterilization and renewal. The imaging device head 812 may further comprise a user input panel 820 having buttons 821 and 822. Additional, buttons may be provided and the functionality of the buttons can be customized for a given procedure and or a given operator. The control panel 820 may be internally connected to other circuitry of the imaging device head 812 by an electrical connector 826.

As illustrated further in the embodiment of FIG. 8, the imaging device head 812 may comprise an optical mount system 850, such as a C-mount system for receiving threaded accessories, for example one inch threaded accessories. A window 855 may also be incorporated into the embodiment for facilitating the transmission of light from an optical accessory to an image sensor 875. The image sensor 875 may be mounted to a supporting printed circuit board or supportive substrate 870. An electronic connector 878 may be incorporated to electronically connect the image sensor 875 to a main circuit or main printed circuit board 860. In order to provide heat dissipation from the image sensor 875 and other circuitry, a heat sink 861 may be provided. The heat sink 861 may be physically connected to the image sensor 875 and it may also be connected to the housing 810, such that heat energy can be conducted or transferred to the external portion of the imaging device head 812. The heat sink 861 may be a neutral sensor heat sink exposed externally to ensure the camera head meets cardiac floating (CF) and body floating (BF) ISO standards. An embodiment of the heat sink 861 may be made of aluminum and have fins for added heat transfer surface area. A main wiring harness 882 may be incorporated into a wired tether 880 thereby electrically connecting the components of the imaging device head 812 to a control unit.

The imaging device head 812 may further comprise a memory 888 or memory circuit allowing the storage of data within the imaging device head 812. Data that may be stored or written into memory 888 may include an identifying serial number that uniquely identifies an imaging device. Other data that may be stored or written into memory 888 may include data such as the amount of the time the imaging device has been used, i.e., the hours of operation, or the amount of time the imaging device has been powered on. Data that may be written into memory 888 may include sterilization data or renewal data, representing the working condition of the imaging device. Data that may be stored or written into memory 888 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 888 may be encryption protected so as to avoid tampering or unintended use and foreseeable misuse. It should be noted that a memory may be placed anywhere in the imaging device and not just the imaging device head without departing from the scope of the disclosure. The memory 888 may comprise a permanent or semi-permanent portion allowing varying degrees of data durability.

Figure 9:
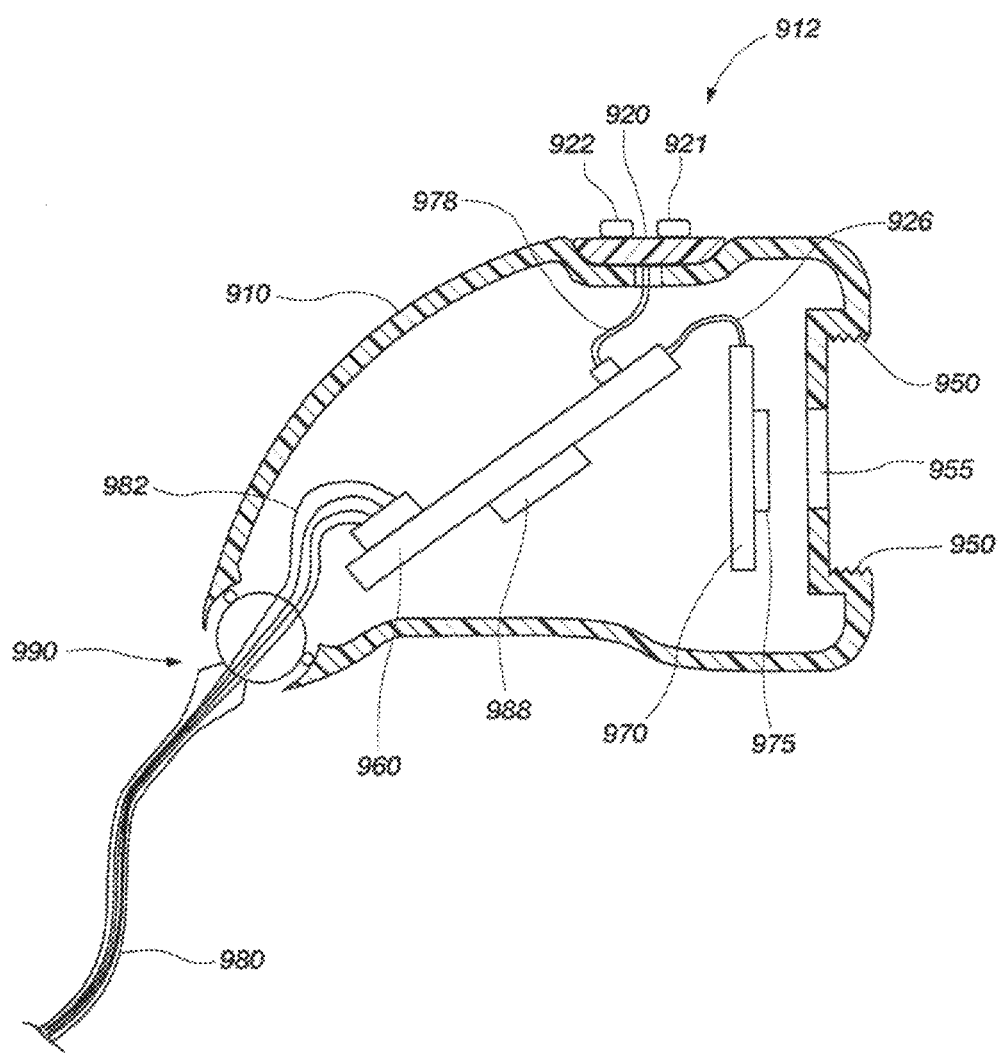
FIG. 9 is a cross-sectional view of an embodiment of an imaging device head made in accordance with the teachings and principles of the disclosure.

Illustrated in FIG. 9 is a cross-sectional view of an embodiment of an imaging device head 912. The imaging device head 912 may comprise a housing 910 made of a suitably rigid material such as plastic or metal. The housing 910 may be sealed against fluids and gases so as to protect the internal circuitry and provide a suitable surface for sterilization and renewal. The imaging device head 912 may further comprise a user input panel 920 having buttons 921 and 922. Additional, buttons may be provided and the functionality of the buttons can be customized for a given procedure and or a given operator. The control panel 920 may be internally connected to other circuitry of the imaging device head 912 by an electrical connector 926.

As illustrated further in the embodiment of FIG. 9, the imaging device head 912 may comprise an optical mount system 950, such as a C-mount system for receiving threaded accessories, for example one inch threaded accessories. A window 955 may also be incorporated into the embodiment for facilitating the transmission of light from an optical accessory to an image sensor 975. The image sensor 975 may be mounted to a supporting printed circuit board or supportive substrate 970. An electronic connector 978 may be incorporated to electronically connect the image sensor 975 to a main circuit or main printed circuit board 960. In order to provide heat dissipation from the image sensor 975 and other circuitry, a heat sink may be provided, similar to the heat sink provided in FIG. 8. The heat sink may be physically connected to the image sensor 975 and it may also be connected to the housing 910, such that heat energy can be conducted or transferred to the external portion of the imaging device head 912. A main wiring harness 982 may be incorporated into a wired tether 980 thereby electrically connecting the components of the imaging device head 912 to a control unit.

The imaging device head 912 may further comprise a memory 988 or memory circuit allowing the storage of data within the imaging device head 912. Data that may be stored or written into memory 988 may include an identifying serial number that uniquely identifies an imaging device. Other data that may be stored or written into memory 988 may include data such as the amount of the time the imaging device has been used, i.e., the hours of operation, or the amount of time the imaging device has been powered on. Data that may be stored or written into memory 988 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 988 may be encryption protected so as to avoid tampering or unintended use and foreseeable misuse. It should be noted that a memory may be placed anywhere in the imaging device and not just the imaging device head without departing from the scope of the disclosure. The memory 988 may comprise a permanent or semi-permanent portion allowing varying degrees of data durability.

The imaging device head 912 may comprise a ball joint 990 with a corresponding seal and socket, thereby providing increased mobility between the housing 910 and the tether 980 during articulation of the imaging device by an operator or user.

Figure 10:
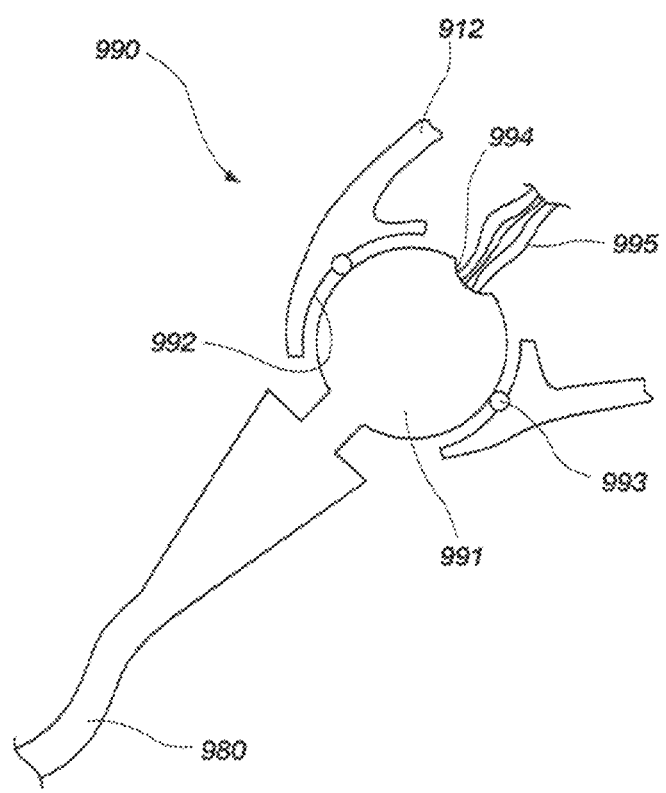
FIG. 10 is a cross-sectional view of an embodiment of an imaging device head having a ball joint made in accordance with the teachings and principles of the disclosure.

With reference primarily to FIG. 10, an embodiment of an imaging device ball joint 990 will be discussed in further detail. FIG. 10 is illustrative of a cross-sectional view of a ball joint 990, which provides greater freedom of articulation for an operator when moving the imaging device head 912 relative to the wiring tether 980. The ball joint 990 may comprise a substantially spherical rotatable portion or ball 991. The ball 991 may be configured to mechanically operate in communication with a corresponding socket 992, such that the ball 991 may substantially freely rotate while being retained within the socket 992. A seal may be provided withing the ball joint 990 by the inclusion of a seal ring 993. The seal ring 993 may also provide mechanical resistence within the ball joint 990. The ball 991 may further include an opening 994 therethrough allowing wiring 995 to pass through the ball joint 990.

Figure 11:
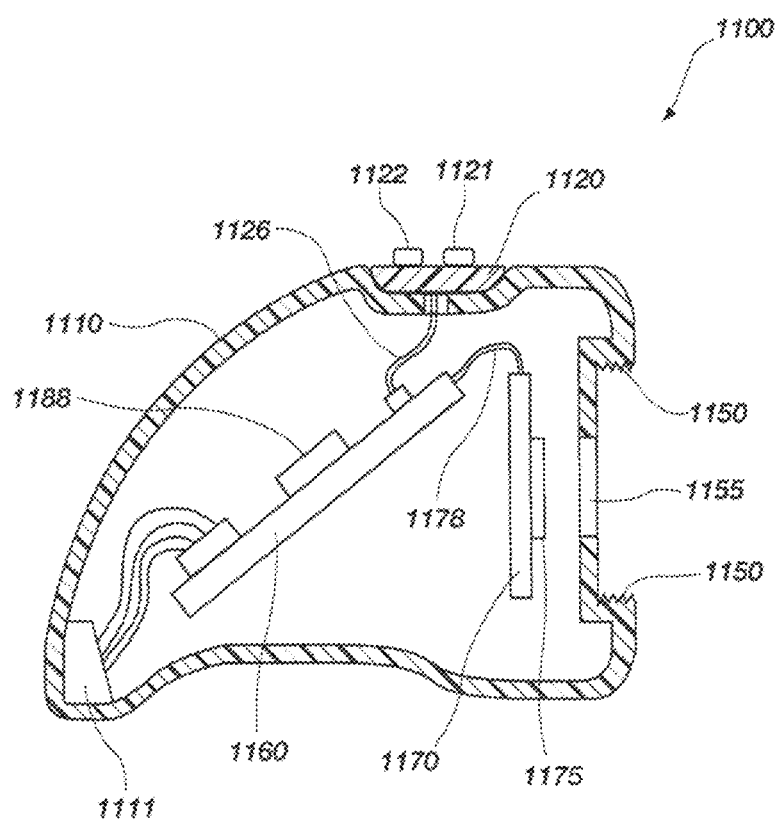
FIG. 11 is a cross-sectional view of an embodiment of an imaging device head made in accordance with the teachings and principles of the disclosure.

With reference to FIG. 11, an embodiment of an imaging device 1100 comprising wireless transmission functionality will be discussed. A cross-sectional view of an embodiment of an imaging device head 1112 is shown in FIG. 11. The imaging device head 1112 may comprise a housing 1110 made of a suitably rigid material such as plastic or metal. The housing 1110 may be sealed against fluids and gases so as to protect the internal circuitry and provide a suitable surface for sterilization and renewal. The imaging device head 1112 may further comprise a user input panel 1120 having buttons 1121 and 1122. Additional, buttons may be provided and the functionality of the buttons can be customized for a given procedure and or a given operator. The control panel 1120 may be internally connected to other circuitry of the imaging device head 1112 by an electrical connector 1126. The imaging device head 1112 may communicate with a control unit by way of wireless transmissions such as Wifi, infrared, bluetooth etc. Other forms of wireless non-tethered connectivity may also be used for providing communication between the imaging device head 1112 and the control unit, including but not limited to, radio frequency from any available spectrum, infrared of any configuration, ultrasonic, and optical. As illustrated further in the embodiment of FIG. 11, the imaging device head 1112 may comprise an optical mount system 1150, such as a C-mount system for receiving threaded accessories, for example one inch threaded accessories. A window 1155 may also be incorporated into the embodiment for facilitating the transmission of light from an optical accessory to an image sensor 1175. The image sensor 1175 may be mounted to a supporting printed circuit board or supportive substrate 1170. An electronic connector 1178 may be incorporated to electronically connect the image sensor 1175 to a main circuit or main printed circuit board 1160. The circuitry of the imaging device head 1112 may electrically be connected to a wireless transceiver 1111 for transmitting and receiving data from a wirelessly configured control unit as illustrated in FIG. 3.

The imaging device head 1112 may further comprise a memory 1188 or memory circuit allowing the storage of data within the imaging device head 1112. Data that may be stored or written into memory 1188 may include an identifying serial number that uniquely identifies an imaging device. Other data that may be stored or written into memory 1188 may include data such as the amount of the time the imaging device has been used, i.e., the hours of operation, or the amount of time the imaging device has been powered on. Data that may be stored or written into memory 1188 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon.

Data representing the above characteristics, or other indicia, of the imaging device may be recorded into memory within the imaging device.

The memory 1188 may be encryption protected so as to avoid tampering or unintended use and foreseeable misuse. It should be noted that a memory may be placed anywhere in the imaging device and not just the imaging device head without departing from the scope of the disclosure. The memory 1188 may comprise a permanent or semi-permanent portion allowing a varying degrees of data durability.

It will be appreciated that the ball joint illustrated in FIGS. 9 and 10 may be used by any embodiment of the disclosure without departing from the spirit or scope of the disclosure. Thus, for example, the ball joint 990 may be used with imaging device head 712, 812, 912, or 1112. Similarly, it will be appreciated that the heat sink 861 (illustrated in FIG. 8) may be used by any embodiment of the disclosure without departing from the scope of the disclosure.

Referring now to FIG. 12 an embodiment of a system for acquiring imagery in a sterilized environment will be discussed. The system may comprise an imaging device 1201 having a memory 1202, an image sensor 1204, and supporting circuitry 1206, including a processor. The imaging device 1201 may be an active device and may comprise a processor, a micro-processor or micro controller, a field programmable gate array (FPGA), active circuit, or a complex programmable logic device (CPLD). The system may further comprise and control unit 1220 having a processor 1221, time circuit or realtime clock 1222, a counting or incrementing circuit 1224 and a control unit memory 1226. The components will generally be provided in a housing, but are shown hear in block diagram form for simplicity and discussion purposes. It is contemplated that any of the above circuits can operate from either a control unit or an imaging device.

Figure 13:
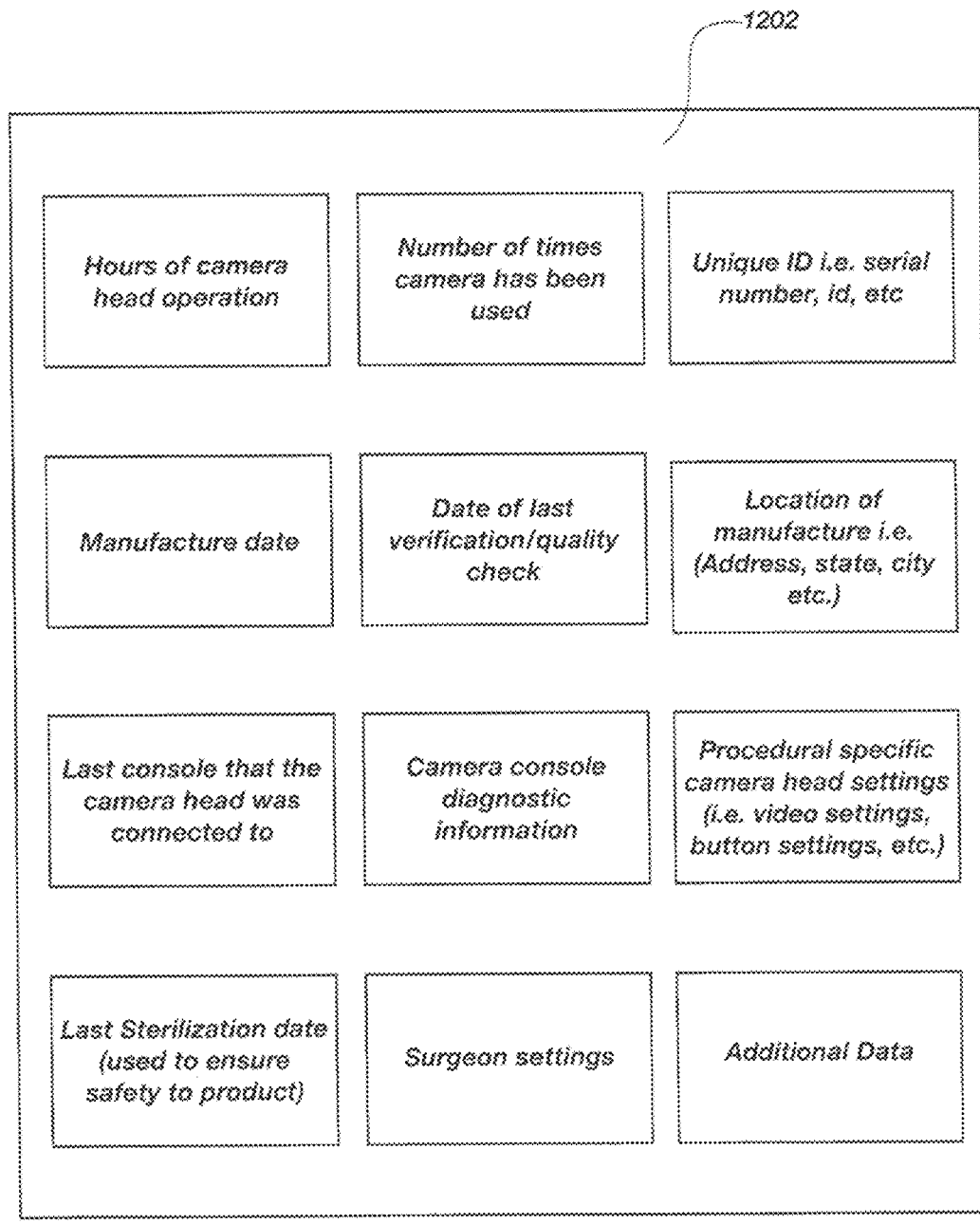
FIG. 13 is a schematic diagram of a memory of an embodiment of an imaging system made in accordance with the teachings and principles of the disclosure.

As can be seen in FIG. 13 the memory 1202 of the imaging device 1201 may comprise the following arrays of data storage:

a. Hours of camera head operation;
b. Number of times camera has been used;
c. Unique identification i.e. serial number, id, etc.;
d. Manufacture date;
e. Date of last verification/quality check;
f. Location of manufacture i.e. (Address, state, city etc.);
g. Last console that the camera head was connected to;
h. Camera console diagnostic information;
i. Procedural specific camera head settings (i.e. video settings, button settings, etc.);
j. Last Sterilization date (used to ensure safety to product); and
k. Surgeon or user settings.

Additional data may be stored within the memory 1202 that would enhance the imaging device and is considered to be within the scope of the disclosure.

Figure 14:
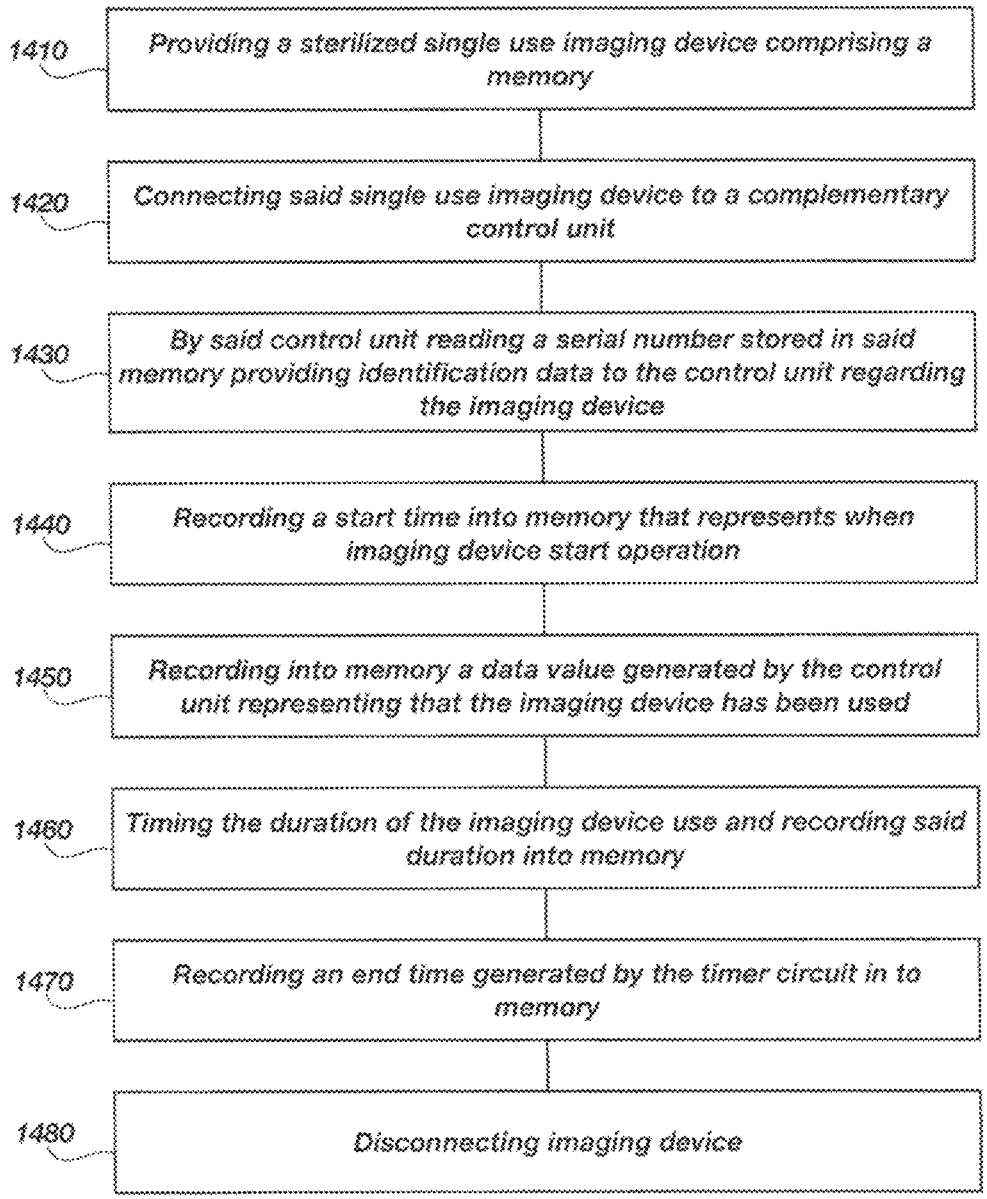
FIG. 14 illustrates an embodiment of a method of using an imaging system in accordance with the teachings and principles of the disclosure.

With reference to FIG. 14, a method of using an imaging system consistent with the embodiments disclosed herein will be discussed. In use, a sterilized single use imaging device 1201 will be provided that may comprise memory 1202 at 1410. At 1420 a user may connect the single use imaging device 1201 to a complementary control unit 1220 both electronically and physically. At 1430 the control unit 1220 may initiate a process of reading memory 1202 and registers the serial number of the imaging device 1201. At 1440 the system causes a value to be recorded into memory 1202 indicating that the imaging device 1201 has been used. At 1450 the system records into memory 1202 the date and time the imaging device 1201 is connected to the control unit 1220. At 1460 a timing process is initiated by the control unit from the base line time recorded at 1450 and tracks or times the duration that the imaging device 1201 is used and the duration is recorded into memory 1202 at 1470. After use, the imaging device 1201 is disconnected from the control unit 1220 at 1480 and then discarded for renewal or reclamation.

Figure 15:
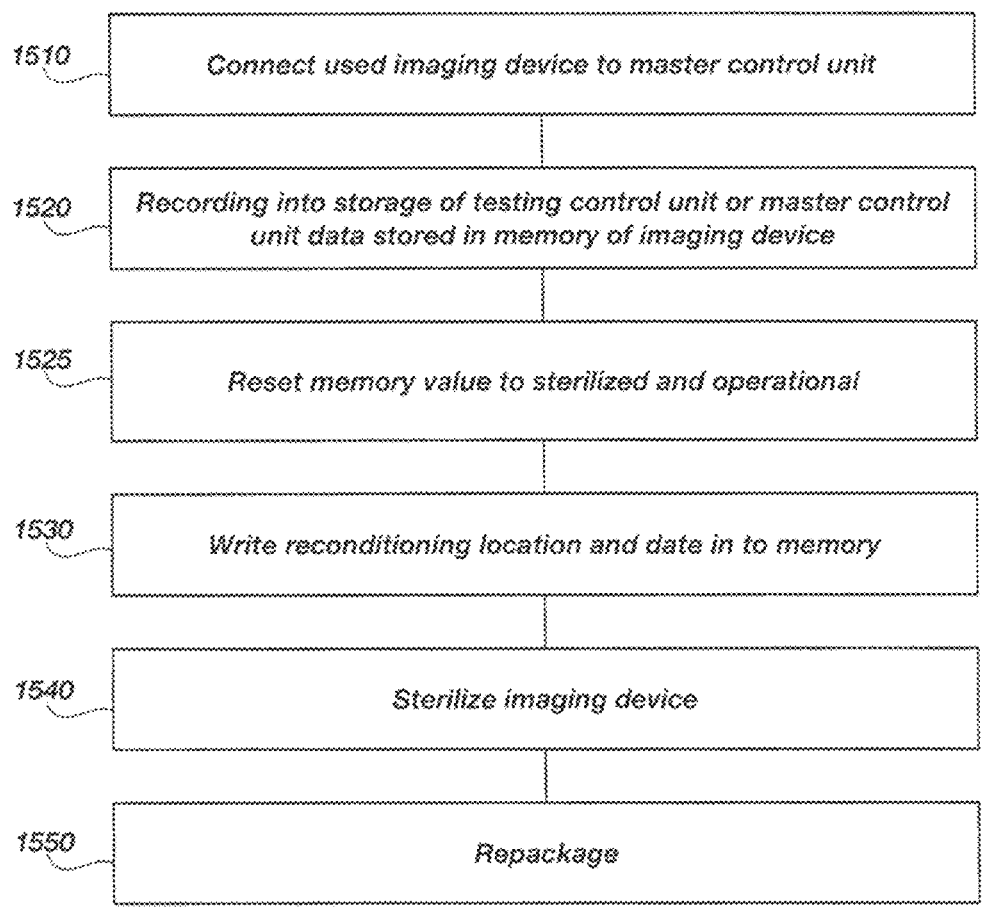
FIGS. 15 and 15A illustrate embodiments of a method of renewing and reclaiming an imaging device in accordance with the teachings and principles of the disclosure.
Figure 15A:
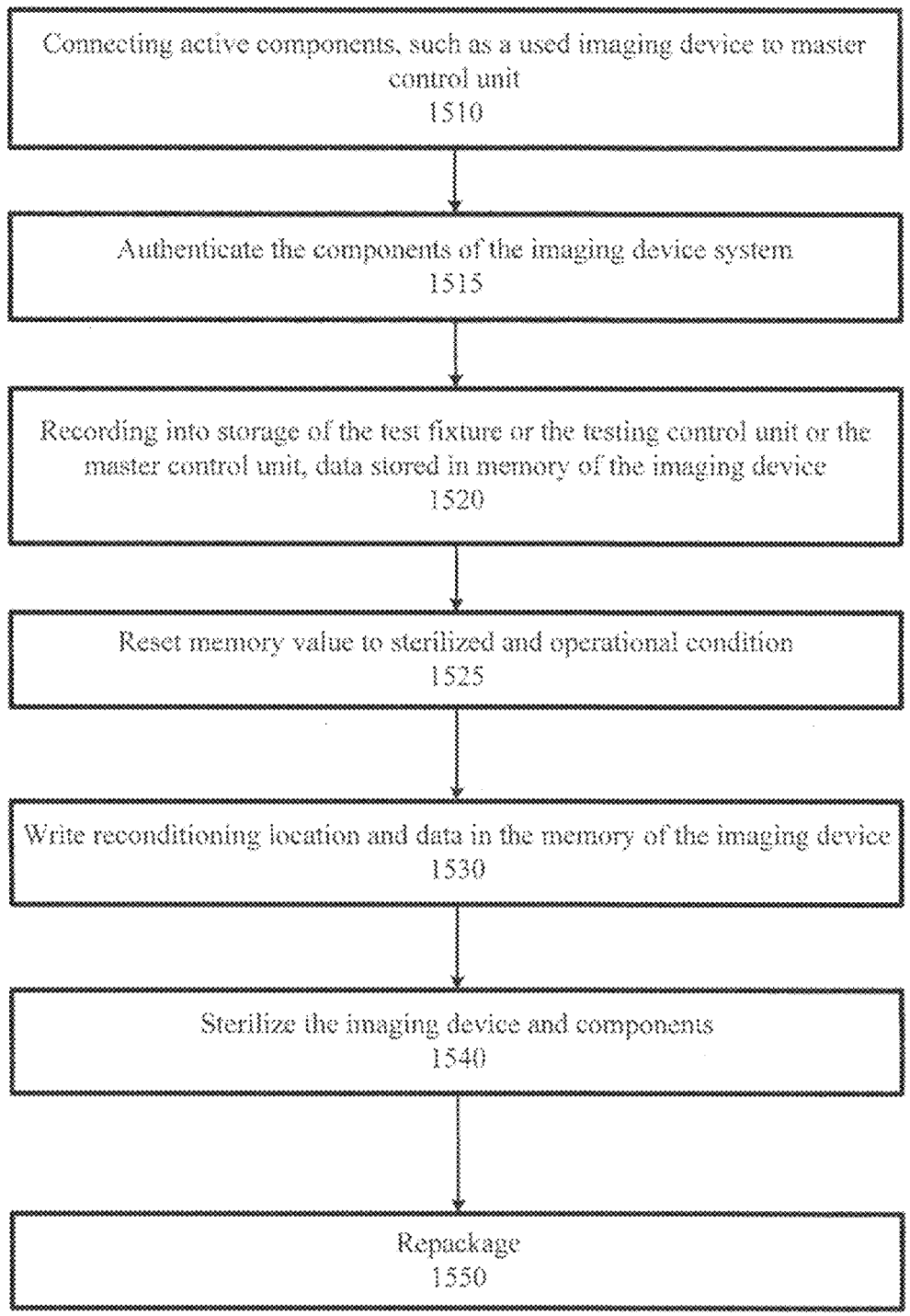

Referring now to FIGS. 15 and 15A, a method of renewing and reclaiming a single use imaging device 1201 will be discussed. At 1510 the imaging device 1201 may be connected to a testing control unit or a master control unit. At 1515 the components of the imaging system may be authenticated according to the teachings and principles of the disclosure (see discussion in relation to FIG. 30 below). At 1520 the testing control unit or master control unit causes the data stored in memory 1202 to be recorded into storage on the testing control unit or master control unit as stored, in order for the specific imaging device 1201 to be renewed. At 1525 a value is placed in memory 1202 indicating that the imaging device has been renewed and is ready for use such that when connected to another control unit for use it will operate. The location and date of the renewal may then be recorded into memory 1202 at 1530. At 1540 the imaging device 1201 can be sterilized and (at 1550) placed in a protective sterilized package.

Figure 16:
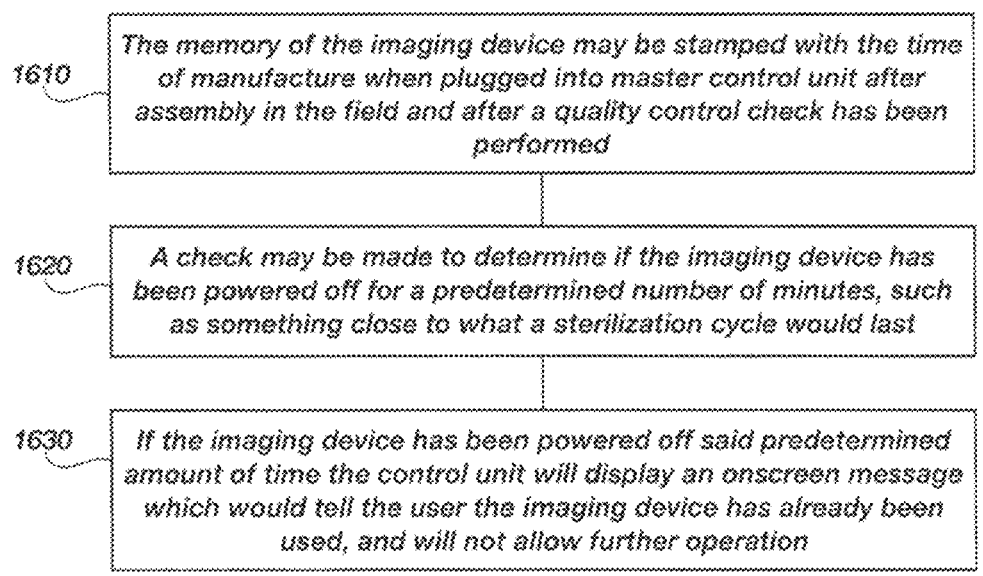
FIG. 16 illustrates an embodiment of a method of use in accordance with the teachings and principles of the disclosure.

With reference to FIG. 16 an alternative embodiment of a method of use will be discussed illustrating safety settings of the embodiment. At 1610 the memory imaging device head may be stamped with time of manufacture when it is plugged into the master control unit or master console after assembly in the field, i.e., in an operating room, and after a quality control check has been performed. At 1620 a check may be made to determine if the imaging device has been powered off for a predetermined number of minutes, such as a time frame that is close to what a typical sterilization cycle would last. At 1630, if the imaging device has been powered off the predetermined amount of time the control unit will display an onscreen message telling the user the imaging device has already been used, and will not allow further operation, such that no image will be produced through video feed. This feature will ensure the imaging device, i.e., the camera, will not be used more than one time per sterilization cycle. This feature also protects the patient and the doctor from an invalid or unsafe use and foreseeable misuse.

Figure 17:
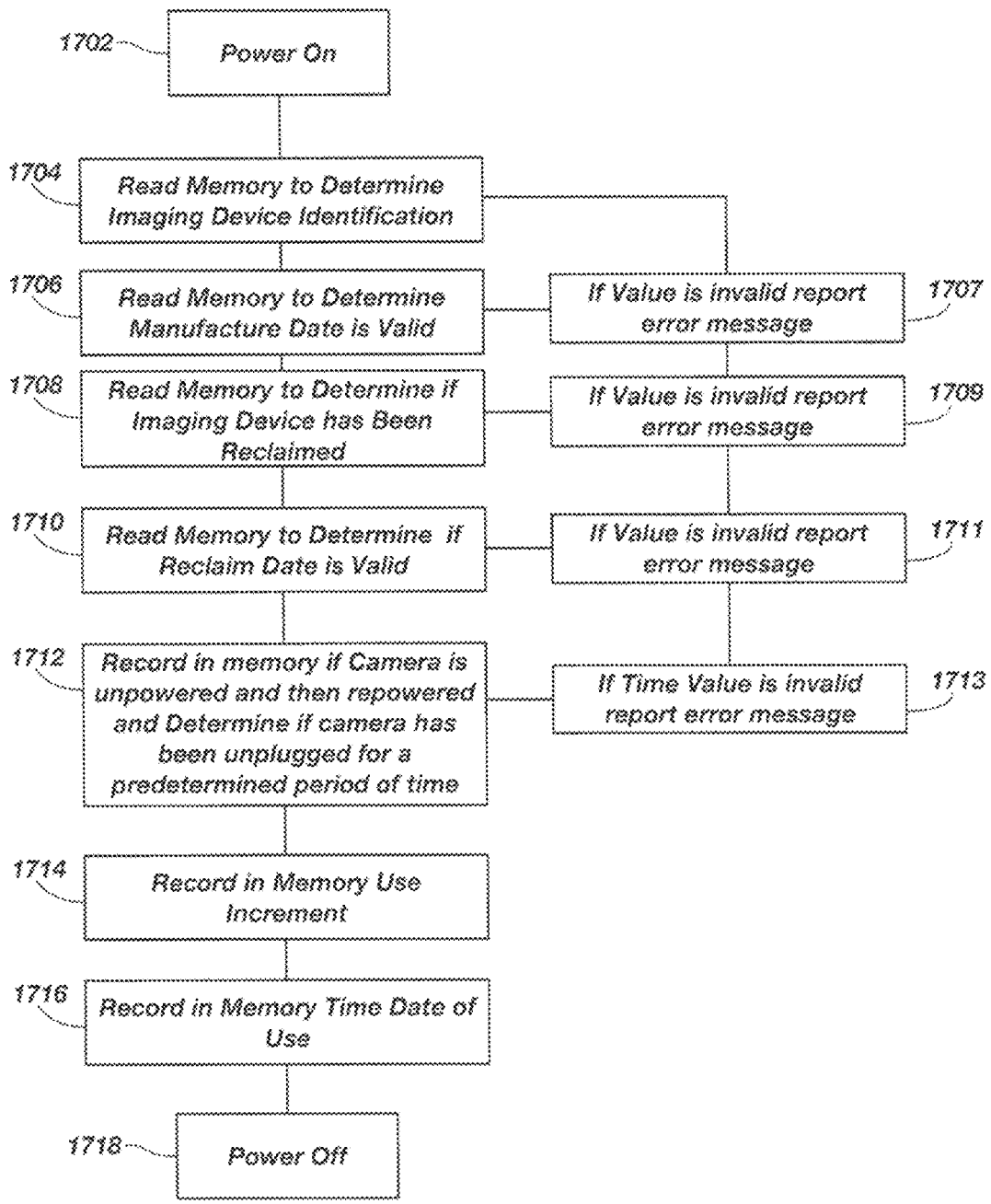
FIG. 17 illustrates an embodiment of a method of use according to the teachings and principles of the disclosure.

Referring to FIG. 17 an embodiment of a method of use will be discussed. During use, an imaging device may be connected to a control unit. Upon connection, an electronic communication connection is formed between the imaging device and the control unit. At 1702 the imaging device may be powered on by power supplied by the control unit. At 1704 a processor in the control unit may cause data regarding imaging device identification that may be stored in a memory within the imaging device to be read. At 1706 a processor in the control unit may cause data regarding the manufacturing date of the imaging device to be read from memory within the imaging device. The processor in the control unit may then compare the data to a predetermined data value range. At 1707 an error message may be displayed if the read data is outside the predetermined data value range and the imaging device will be stopped from operating. At 1708 a processor in the control unit may cause data regarding the reclamation of the imaging device to be read from memory within the imaging device. The data regarding reclamation of the imaging device may include data representing whether or not the imaging device has been previously used. The processor may then compare the data to a predetermined data value range. At 1709 an error massage may be displayed if the read data is outside the predetermined data value range and the imaging device will be stopped from operating. At 1710 a processor in the control unit may cause data regarding the reclamation date of the imaging device to be read from memory within the imaging device. The processor may then compare the data to a predetermined data value range. At 1711 an error massage may be displayed if the read data is outside the predetermined data value range and the imaging device will be stopped from operating. At 1712 a processor in the control unit may cause usage information of the current procedure to be monitored to note whether imaging device has been unpowered for a predetermined period of time and then re-powered. If this condition occurs it is possible that the imaging device has been tampered with or that an attempt has been made to sterilize the imaging device and use it a second time. The predetermined period of time may correspond to the amount of time a typical sterilization process would normally take. The processor then compares the data to a predetermined data value range. At 17013 an error massage may be displayed if the data read is outside the predetermined data value range and the imaging device will be stopped from operating. At 1714 a processor in the control unit may cause a value to be placed in memory in the imaging device indicating that the imaging device has been used. At 1716 a processor in the control unit may cause the date and time of use to be recorded in memory in the imaging device. Additional information may be recorded into the memory of the imaging device such as, for example, duration of use, procedure settings, and user settings and any other data suitable for recording to memory. The imaging device may be disconnected from the control unit and thereby powered off at 1718.

Figure 18:
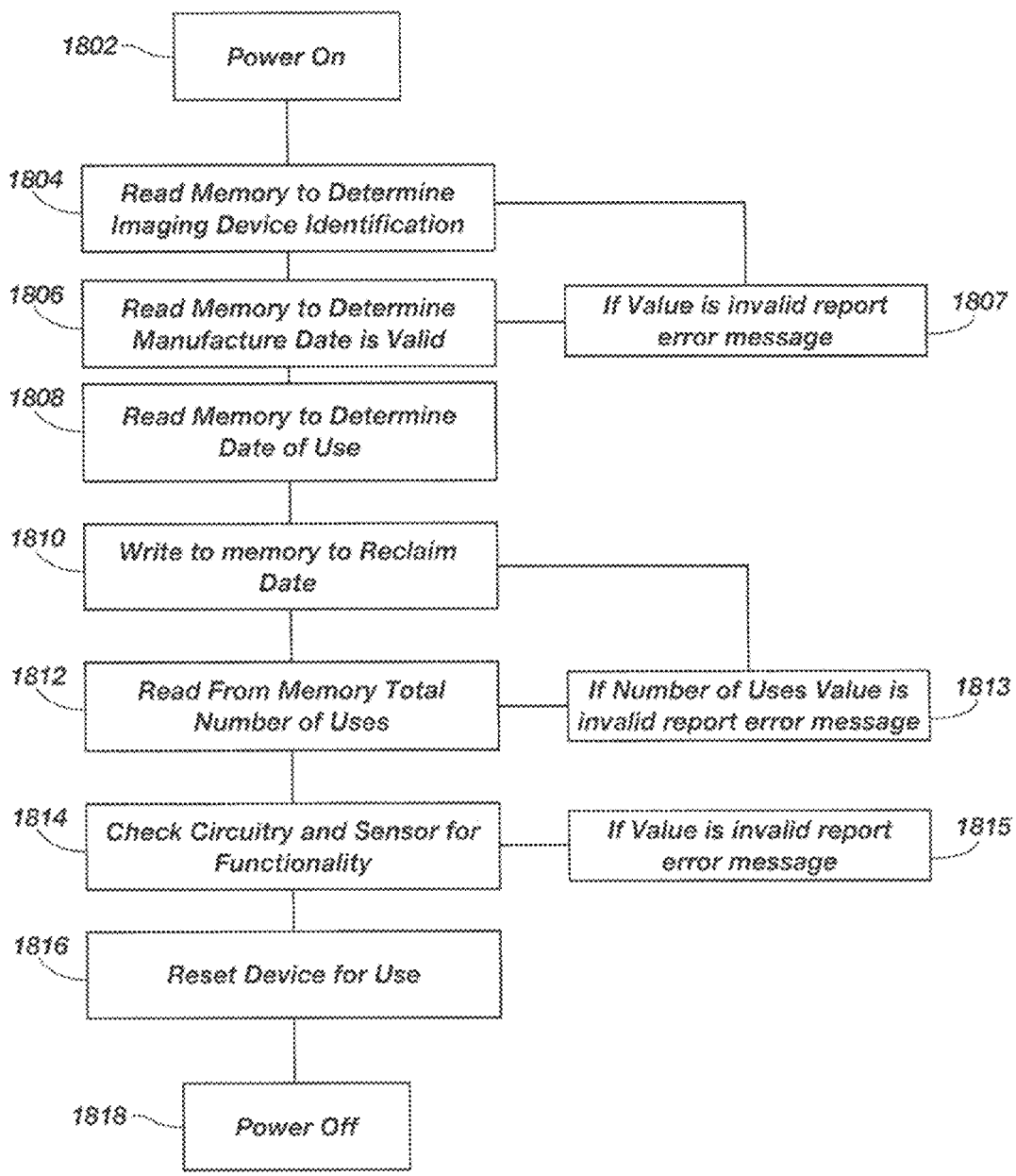
FIG. 18 illustrates an embodiment of a method of reclaiming an imaging device after use according to the teachings and principles of the disclosure.

Referring now to FIG. 18 a method of reclaiming an image device after use will be discussed. It should be noted that a single use imaging device may comprise the durability to be used a plurality of times, however sterilization requirements may prevent an imaging device from being used more than once without a process for reclaiming the imaging device, thereby returning it to a sterilized condition. A method of reclamation for an imaging device may comprise the process of powering on the imaging device at 1802, when the imaging device is electrically connected to a control unit. At 1804 a processor in the control unit may cause data representing identification information for the imaging device to be stored in storage in the control unit. A control unit may be a master control unit configured for reclaiming the imaging devices. The master control unit may track a plurality of imaging devices thereby keeping a catalog of associated information such as use and condition of the device or devices. At 1806 a processor in the control unit may cause that data representing a manufacturing date to be read and compared to a predetermined value or range of values. If the read data is out of the predetermined range value, an error report may be issued at 1807. At 1808 a processor in the control unit may cause data representing use data written in memory of the imaging device to be read and recorded into storage in the control unit. At 1810 a processor may cause data representing a date and time of reclamation to be recorded into memory in the imaging device. At 1812 a processor in the control unit may cause that data representing the number of uses of the imaging device to be read and recorded into storage in the control unit. The processor may compare the read data to a predetermined value or range of values to determine whether the imaging device is fit for continued use. If the predetermined value is exceeded an error message may be displayed (at 1813) and the imaging device may be retired. At 1814 a processor in the control unit may initiate a test or quality control check of all the circuitry in the imaging device to ensure that the device is functional. At 1815 it may be determined that the imaging device failed the quality control check and an error massage may be displayed. At 1816 the imaging device can be reset for use. The resetting process may comprise writing data to the memory of the imaging device indicating that the imaging device has been reclaimed and sterilized. At 1816 the device may be disconnected from the control unit and physically sterilized and repackaged.

Figure 19:
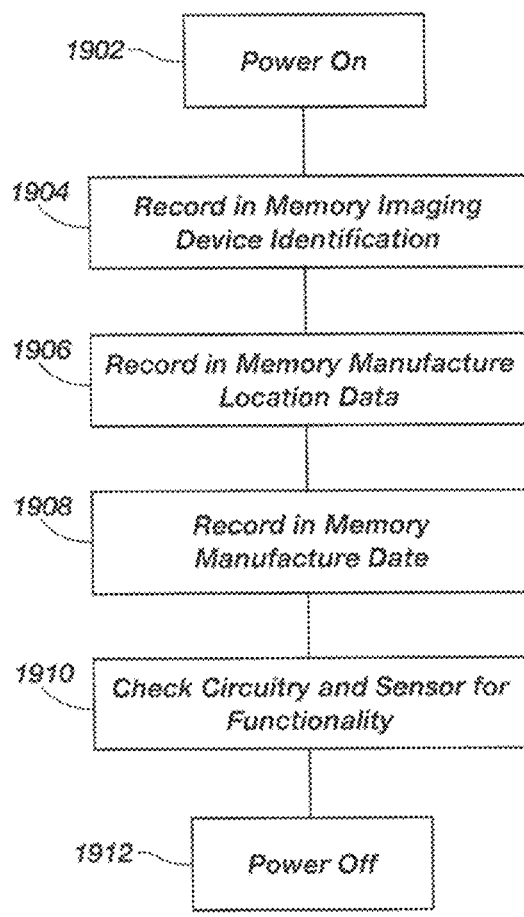
FIG. 19 illustrates an embodiment of a method of making an imaging device for use in a sterilized environment according to the teachings and principles of the disclosure.

With reference primarily to FIG. 19, an embodiment of a method for making an imaging device having memory therein for use in a sterilized environment will be discussed. At 1902 an imaging device may be powered on upon being connected to a control unit. The control unit may be a master control unit configured for the manufacturing process. At 1904 a processor in the control unit may cause that data representing an identification serial number for the imaging device to be written into memory of the imaging device. At 1906 a processor in the control unit may cause that data representing the location of manufacture be recorded to memory in the imaging device. At 1908 a processor may cause that data representing the date of manufacture may be recorded into memory on the imaging device. At 1910 a processor in the control unit may initiate a test or quality control check of all the circuitry in the imaging device to ensure that the device is functional. At 1912 the imaging device may be unplugged from the control and sterilized for packaging.

Referring to an embodiment illustrated in FIG. 20, a system having a security code or some other means of identifying, and validating for use, an imaging device by a control unit, in order to verify that the imaging device is authorized for use will now be described. A validating security code or procedure of validation may be distributed to control units from a central database over the internet, by direct transfer from portable storage device such as USB device containing memory, another computer, or other storage device.

Figure 20:
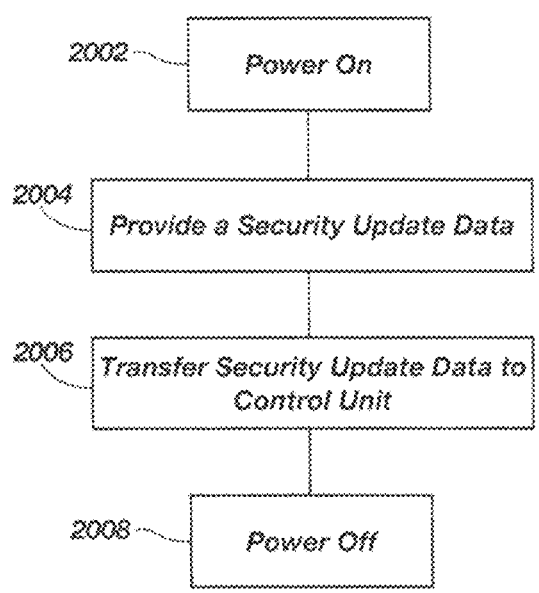
FIG. 20 illustrates an embodiment of a method for updating an imaging device system.

With reference to FIG. 20, an embodiment of a method for providing updates with in a medical imaging system will be discussed. At 2002 a control unit may be powered on to receive a security update. At 2004 security update data may be provided comprising validation codes that correspond to imaging devices to be connected to the control unit. Such validation codes may enable the system to insure that users of the system may be prevented from using imaging devices that have been selected for non-use by a manufacturer or distributor. Selection criteria for non-use may include safety considerations, recall considerations, anti counterfeit measures, and sales and contract considerations. At 2006 the data may be transferred into storage or memory of the control unit in order to provide that data for later comparison to security codes provided by imaging devices. It is within the scope of this disclosure to include all means for transferring data, including but not limited to, transmission over a network, transfer via on site transmission from a storage medium that is portable, such as a disk, memory drive, or short distance wireless transmission. At 2008 the system may be powered off.

Figure 21:
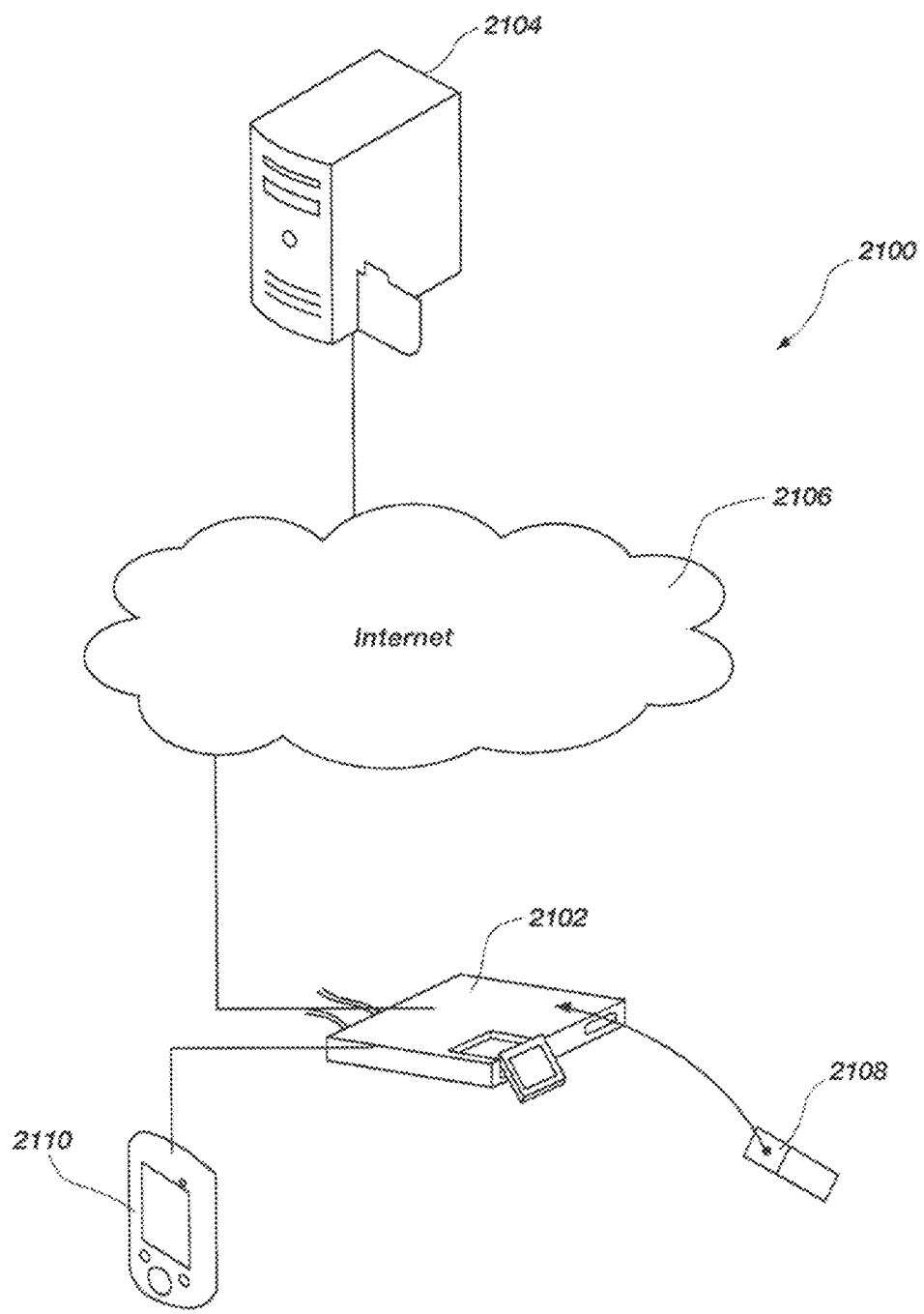
FIG. 21 illustrates an embodiment of a system for providing updates to an imaging system.

With reference primarily to FIG. 21, an embodiment of an imaging system have the feature of updating data will be discussed. An imaging system 2100 may comprise a control unit 2102 and a data server 2104. The control unit 2106 may be electronically in communication with the data server 2104 over a network such as the internet 2106. The control unit 1202 may receive update data over the internet 2106 from data server 2104. The control unit 2102 may also receive update data directly from a memory transfer device 2108 such as a memory stick, thumb drive, jump drive, hard drive, optical disk to name a few. The control unit 2102 may also receive update data from another computer or portable device 2110 such as a PDA or laptop that is presented to the control unit 2102 on site. Data transfer may be made with a physical connection and or by a wireless transfer of data.

Figure 22:
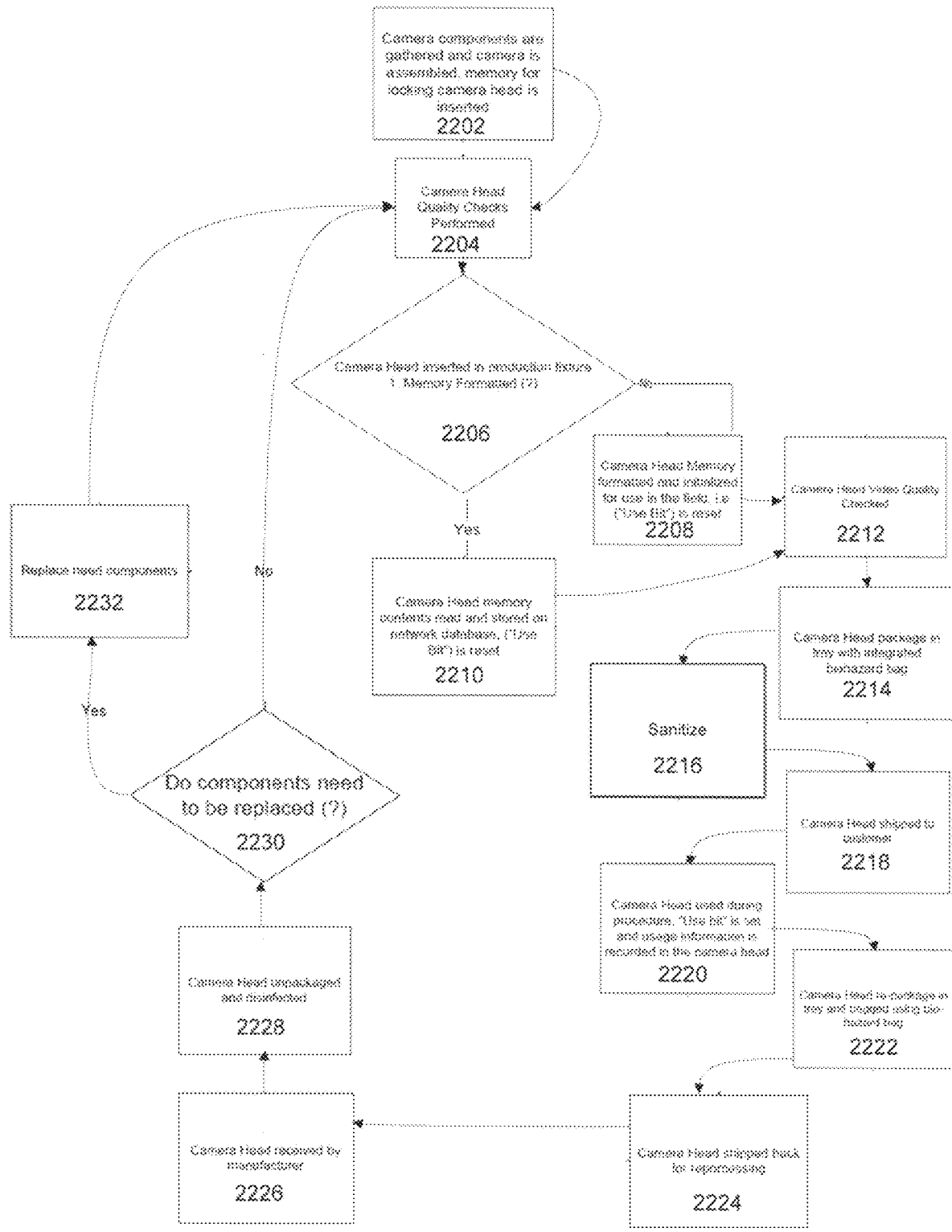
FIG. 22 illustrates an embodiment of a system for the manufacture and reprocessing of a surgical imaging device in accordance with the teachings and principles of the disclosure.

FIG. 22 illustrates an embodiment of a system and method for the manufacture and reprocessing of a surgical camera head or imaging device. Reprocessing may represent the reclaiming or recycling of a used surgical camera head and any associated accessories or components of said surgical camera head and may be referred to individually or collectively herein as an imaging device or a camera head. At 2202 the camera head components are assembled into a working unit having memory. At 2204 the assembled camera head is checked for proper operation and quality to ensure the assembled camera head passes a pre-determined minimum standard. At 2206 the camera head may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2208. If the production control unit determines that data and control values in the memory indicate that the camera is operational or has not been used, the data in the memory will be recorded and stored in a data base while a value or values allowing it to function will be written in to the memory of the camera head at 2210.

At 2212 the camera head may be tested for video quality and other operational standards. The inspection and testing of video quality and other operational standards may include a visual inspection of the video/image quality against a known, acceptable image standard. It will be appreciated that this procedure may be automated, such that if the image does not meet a certain pre-determined quality standard the on screen check will return with a "use or no-use" or "go or no-go" on screen reply or signal.

At 2214 the camera may be packaged in a container, such as a tray, pouch, bag or the like, which may be sterilized along with the components within the container. Such containers may provide the ability to sanitize the camera head while inside the container. This package or container of components may then be sanitized or sterilized as noted at 2216. It will be appreciated that in an embodiment, the components included in the container, such as a tray, pouch, bag or the like, may also include a biohazard bag or sanitation bag. The biohazard bag may be used after an imaging device and related components have been used or otherwise contaminated to return the used or contaminated imaging device, along with any components, to a reprocessing center or agent for disinfection and further reprocessing treatment.

At 2216 the packaged camera head may then be sanitized or sterilized. It will be appreciated that there are many methods for sanitizing, sterilizing or otherwise eliminating (killing) transmissible agents, such as fungi, bacteria, viruses, bacterial spores, etc. from surgical tools and equipment. Such methods are within the scope of the disclosure. Sterilization may be accomplished using one or more of the following heat, chemicals, irradiation, and high pressure systems. Examples of the sanitization or sterilization methods may include ethylene oxide, gamma radiation, chemicals and autoclave systems.

At 2218, the imaging device, i.e., camera head and any accompanying components, may be further packaged and shipped to an end user. The camera head may then be used for a surgical procedure where during the procedure a camera control unit writes to the memory in the camera head where a use value or use bit may be set at 2220. After use or contamination, the camera head may be placed in a return shipping container suitable for biohazard shipping at 2222 and shipped to a processing facility or manufacturer at 2224. At 2226 the processing facility or manufacturer may receive the used or otherwise contaminated camera head and, at 2228, the camera head may be unpackaged and disinfected for further processing. It will be appreciated that the disinfection process is for worker safety where handlers of the used or otherwise contaminated camera head wear protective clothing, such as gloves and gowns. The disinfection process may include chemical treatment of the used or otherwise contaminated imaging device or camera head to meet low-level or other appropriate governmental standards for disinfection. Various chemicals may be used for the initial disinfection process and may include alcohols, aldehydes, and oxidizing agents. It will be appreciated that other disinfection processes may be used to initially treat the used or otherwise contaminated camera head without departing from the scope of the disclosure.

At 2230 the camera head may be inspected to determined whether components need to be replaced. If it is determined that some components of the camera head need to be replaced, then at 2232 the faulty components will be replaced. For example, components that may be replaced include cables, imaging device connectors, and buttons. However, it should be noted that during this inspection all components may be replaced on an as needed basis. After the faulty components have been replaced at 2232, the camera head may be checked for quality and functionality at 2204, and then further processed in accordance to the illustrated system.

It will be appreciated that the above system or method for the manufacture and reprocessing of a surgical camera head or imaging device may include details relating to the camera head itself or the various processes within each step noted, which may be utilized by any of the embodiments disclosed herein and such details are incorporated into each of the embodiments.

Figure 23:
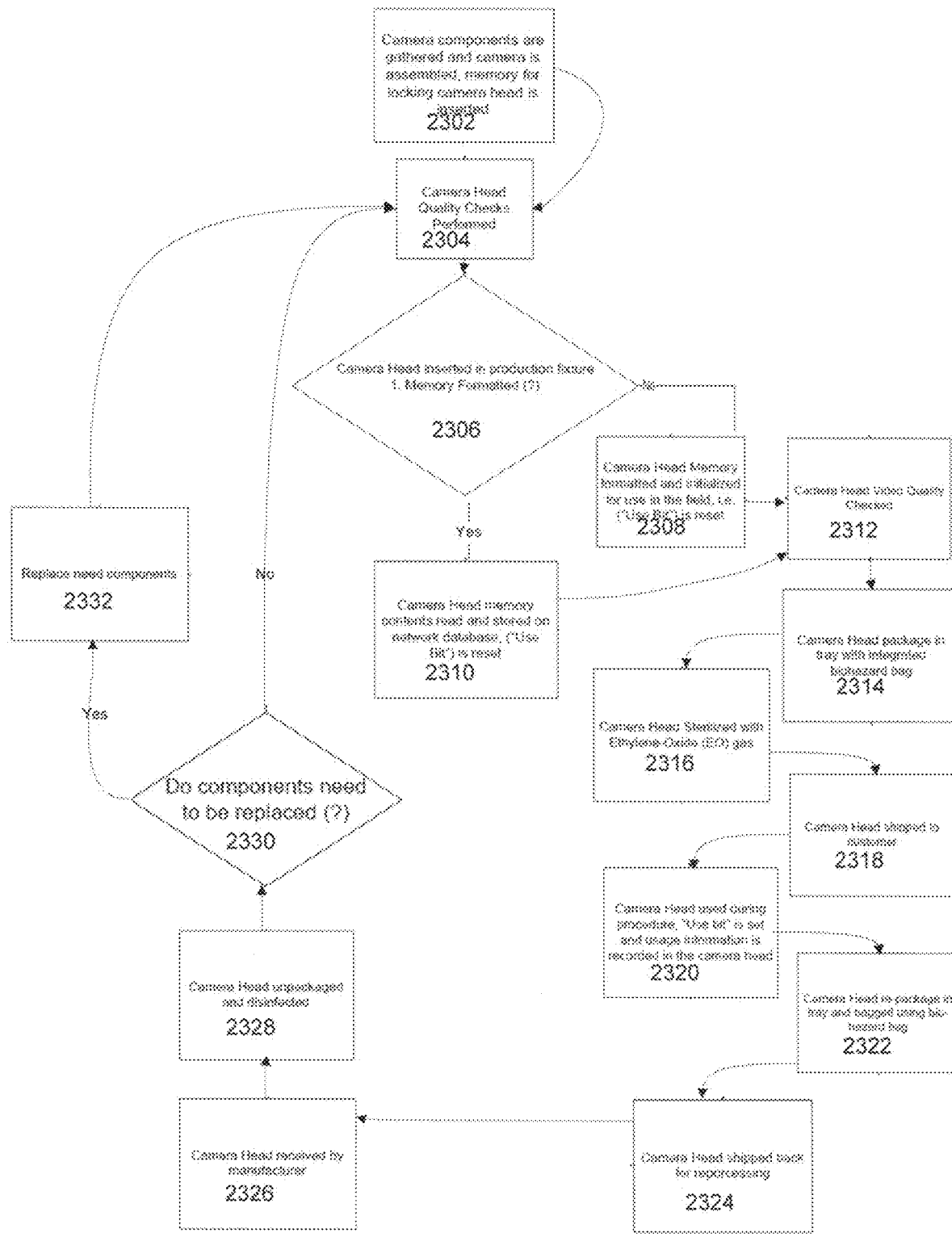
FIG. 23 illustrates an embodiment of a system for the manufacture and reprocessing of a surgical imaging device made in accordance with the teachings and principles of the disclosure.

FIG. 23 illustrates an embodiment of a system for the manufacture and reprocessing of a surgical camera head or imaging device. Reprocessing may represent the reclaiming or recycling of a used surgical camera head and any associated accessories or components of said surgical camera head. At 2302 the camera head components are assembled into a working unit having memory. At 2304 the assembled camera is checked for proper operation and quality. At 2306 the camera head may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2308. If the production control unit determines that data and control values in the memory indicate that the camera is operational or has not been used, the data in the memory will be recorded and stored in a data base while a value or values allowing it to function will be written in to the memory of the camera head at 2310.

At 2312 the camera head may be tested for video quality and other operational standards. At 2314 the camera may be packaged in a biohazard bag or sanitation bag. Such bags may provide the ability to sanitize the camera head while inside the bag. The sanitation process may include or be accomplished using Ethylene-Oxide (EO) gas, or other fluid process corresponding to the properties of said bag or packaging. At 2316 the packaged camera head may then be sanitized. At 2318 the camera head may be further packaged such as in a tray and shipped to an end user. The camera head may be then used for a surgical procedure where during the procedure a camera control unit writes to the memory in the camera head a usage value at 2320. After use the camera head may be placed in a return shipping container suitable for biohazard shipping at 2322 and shipped to a processing facility or manufacturer at 2324. At 2326 the manufacturer or processing facility may receive the used camera head and at 2328 the camera head may be unpackaged and disinfected for further processing. At 2330 the camera head may be inspected to determined whether components need to be replaced. If it is determined that some components of the camera head need to be replaced, at 2332 the faulty components will be replaced. After the faulty components have been replace at 2332, the camera head may be checked for quality and functionality at 2304, and then further processed in accordance to the illustrated system.

Figure 24:
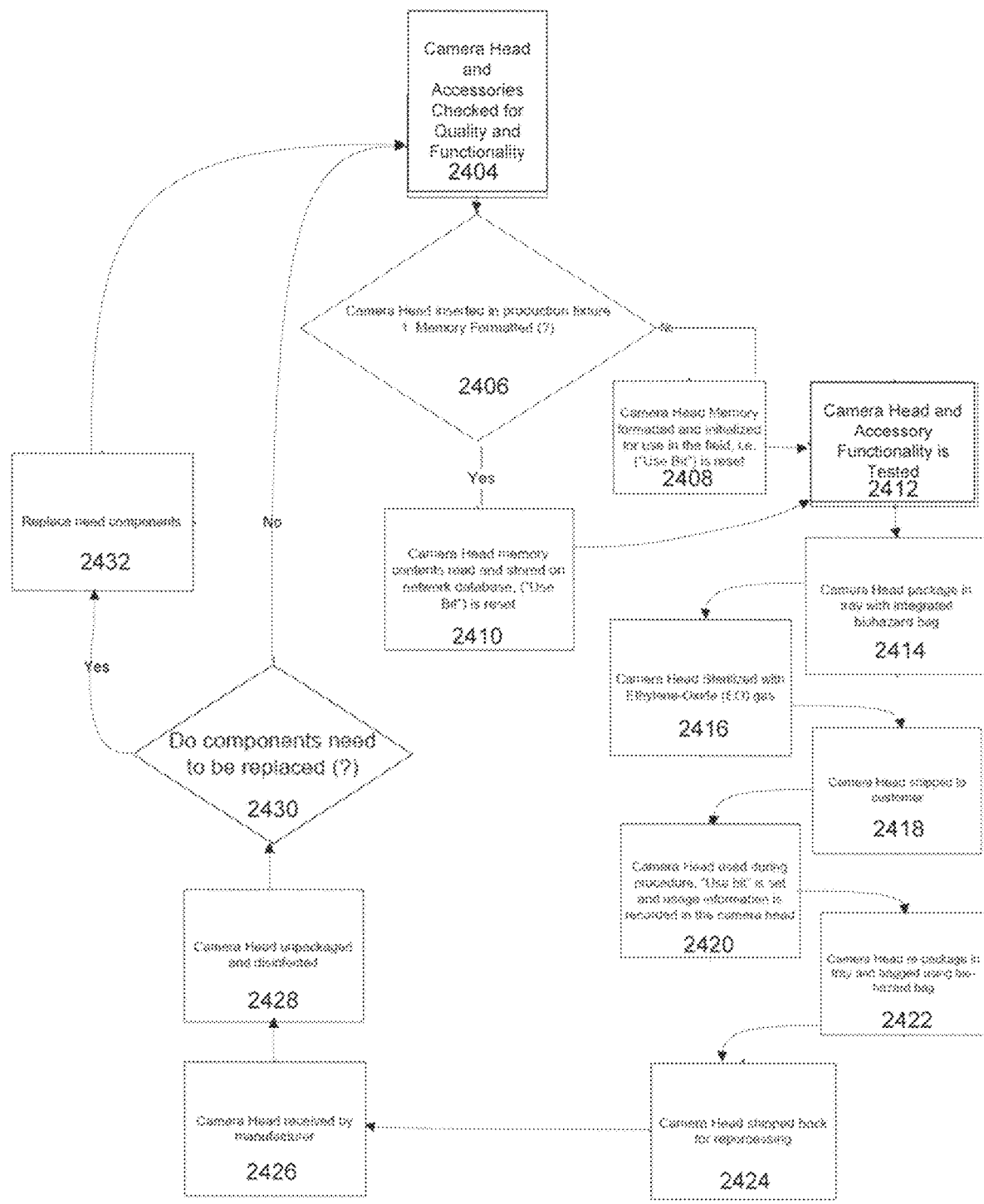
FIG. 24 illustrates an embodiment of a system for the manufacture and reprocessing of a surgical imaging device.

FIG. 24 illustrates an embodiment of a system for the manufacture and reprocessing of a surgical camera head or imaging device. Reprocessing may represent the reclaiming or recycling of a used surgical camera head and any associated accessories or components of said surgical camera head. At 2404 the assembled camera and any accessories are checked for proper operation, quality and functionality. At 2406 the camera head and any associated accessories may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2408. If the production control unit determines that data and control values in the memory indicate that the camera is operational or has not been used, the data in the memory will be recorded and stored in a data base while a value or values allowing it to function will be written in to the memory of the camera head at 2410.

At 2412 the camera head and any associated accessories may be tested for video quality and other operational standards. At 2414 the camera head and any associated accessories may be packaged in a biohazard bag or sanitation bag. Such bags may provide the ability to sanitize the camera head while inside the bag. The sanitation process may include or be accomplished using Ethylene-Oxide (EO) gas, or other fluid process corresponding to the properties of said bag or packaging. At 2416 the packaged camera head and any associated accessories may then be sanitized. At 2418 the camera head and any associated accessories may be further packaged such as in a tray and shipped to an end user. The camera head and any associated accessories may be then used for a surgical procedure where during the procedure a camera control unit writes to the memory in the camera head a usage value at 2420. After use the camera head and any associated accessories may be placed in a return shipping container suitable for biohazard shipping at 2422 and shipped to a processing facility or manufacturer at 2424. At 2426 the manufacturer or processing facility may receive the used camera head and any associated accessories, and at 2428 the camera head and any associated accessories may be unpackaged and disinfected for further processing. At 2430 the camera head and any associated accessories may be inspected to determined whether components need to be replaced. If it is determined that some components of the camera head and any associated accessories need to be replaced, at 2432 the faulty components will be replaced. After the faulty components have been replace at 2432, the camera head and any associated accessories may be checked for quality and functionality at 2404, and then further processed in accordance to the illustrated system.

Figure 25:
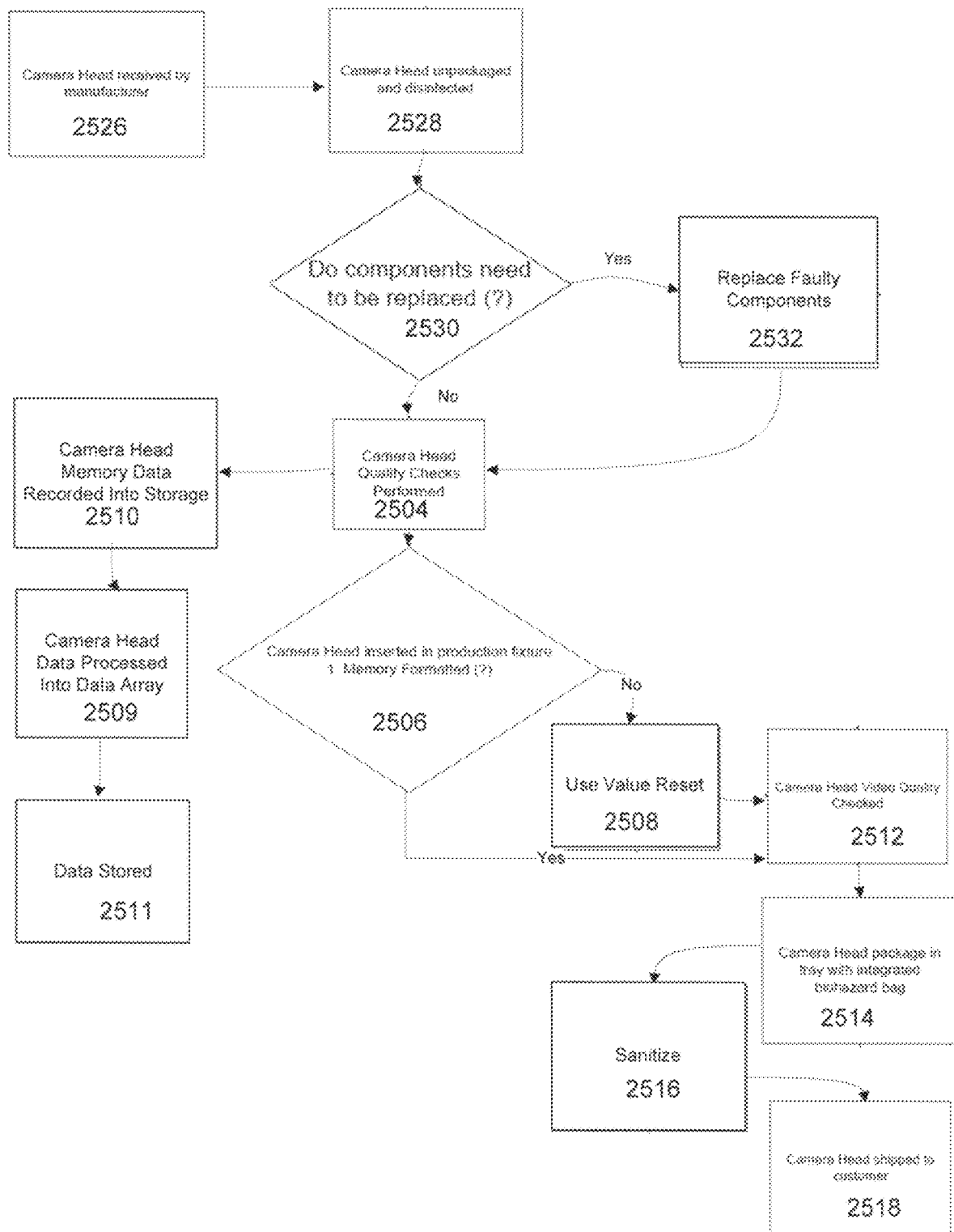
FIG. 25 illustrates an embodiment of a system for the reprocessing of a surgical imaging device.

FIG. 25 illustrates an embodiment of a system for the reprocessing of a surgical camera head or imaging device. Reprocessing may represent the reclaiming or recycling of a used surgical camera head and any associated accessories or components of said surgical camera head. At 2526 the manufacturer or processing facility may receive the used camera head and any associated accessories, and at 2528 the camera head and any associated accessories may be unpackaged and disinfected for further processing. At 2530 the camera head and any associated accessories may be inspected to determined whether components need to be replaced. If it is determined that some components of the camera head and any associated accessories need to be replaced, at 2532 the faulty components will be replaced. After the faulty components have been replace at 2532, the camera head and any associated accessories may be checked for quality and functionality at 2504, and then further processed in accordance to the illustrated system. At 2504 the assembled camera and any accessories are checked for proper operation, quality and functionality. At 2506 the camera head and any associated accessories may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2508. If the production control unit determines that data and control values in the memory indicate that the camera is operational or has not been used, the data in the memory will be recorded and stored in a data base while a value or values allowing it to function will be written in to the memory of the camera head at 2510. A processor within a computer may be employed to read and record into storage data from said camera head at 2509 and the data may be stored for later use at 2511.

At 2512 the camera head and any associated accessories may be tested for video quality and other operational standards. At 2514 the camera head and any associated accessories may be packaged in a biohazard bag or sanitation bag. Such bags may provide the ability to sanitize the camera head while inside the bag. The sanitation process may include or be accomplished using Ethylene-Oxide (EO) gas, or other fluid process corresponding to the properties of said bag or packaging. At 2516 the packaged camera head and any associated accessories may then be sanitized. At 2518 the camera head and any associated accessories may be further packaged such as in a tray and shipped to an end user.

Figure 26:
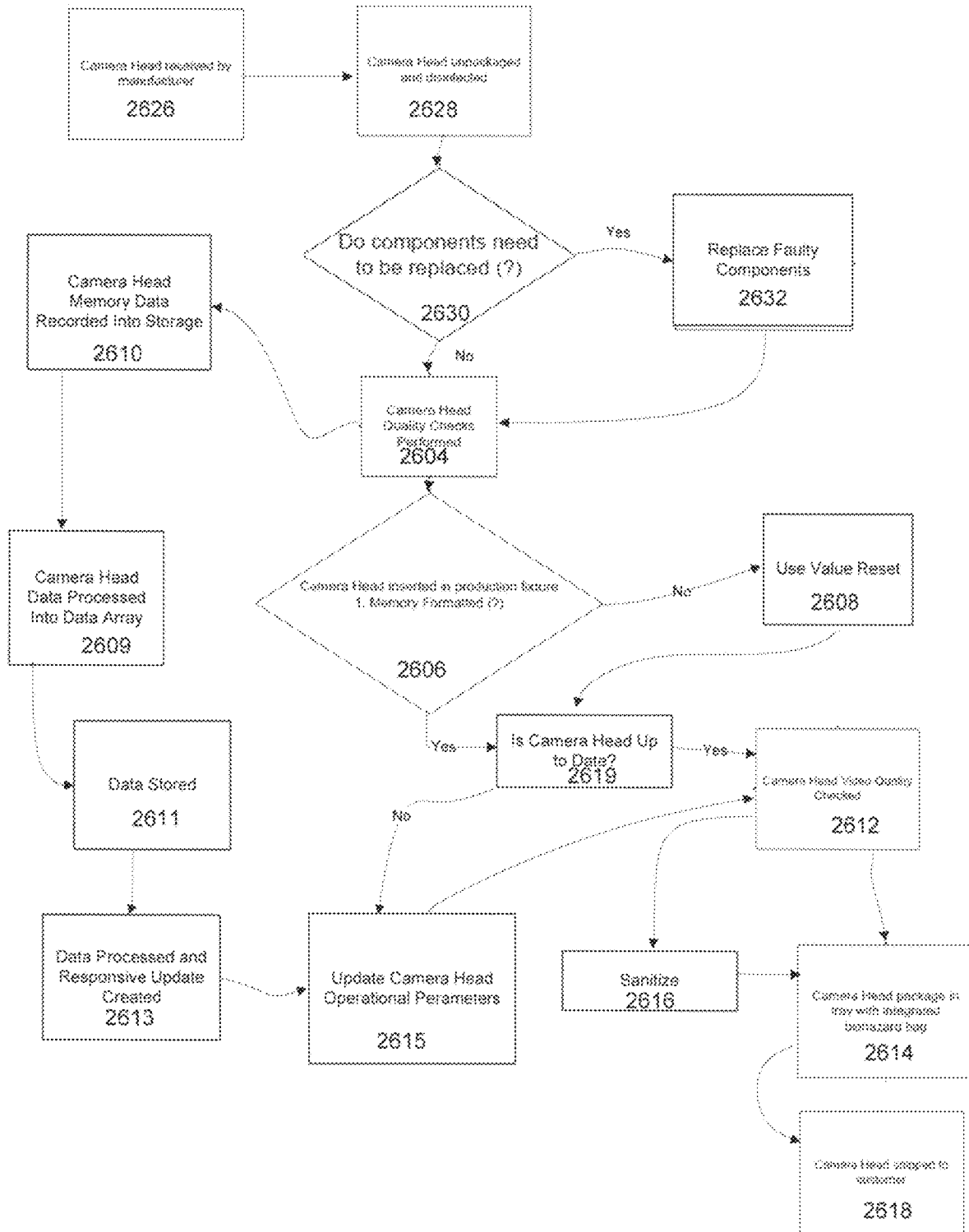
FIG. 26 illustrates an embodiment of a system for the reprocessing of a surgical imaging device and providing updates for said imaging device.

FIG. 26 illustrates an embodiment of a system for the reprocessing of a surgical camera head or imaging device and providing updates for said camera head or imaging device. Reprocessing may represent the reclaiming or recycling of a used surgical camera head and any associated accessories or components of said surgical camera head. At 2626 the manufacturer or processing facility may receive the used camera head and any associated accessories, and at 2628 the camera head and any associated accessories may be unpackaged and disinfected for further processing. At 2630 the camera head and any associated accessories may be inspected to determined whether components need to be replaced. If it is determined that some components of the camera head and any associated accessories need to be replaced, at 2632 the faulty components will be replaced. After the faulty components have been replace at 2632, the camera head and any associated accessories may be checked for quality and functionality at 2604, and then further processed in accordance to the illustrated system. At 2604 the assembled camera and any accessories are checked for proper operation, quality and functionality. At 2606 the camera head and any associated accessories may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2608. If the production control unit determines that data and control values in the memory indicate that the camera is operational or has not been used, the data in the memory will be recorded and stored in a data base while a value or values allowing it to function will be written in to the memory of the camera head at 2610. A processor within a computer may be employed to read and record into storage data from said camera head at 2609 and the data may be stored for later use at 2611.

At 2619 it may be determined whether the operation of the camera head is up to date. At 2613 updates may be created to improve or modify the camera head. The update may be derived from camera head data stored at 2611 and may be responsive to said camera head data. At 2615 the camera head may be updated. Such updates may be written to the memory of the camera head and may be done manually, automatically, at the point of operation or over a network connection.

At 2612 the camera head and any associated accessories may be tested for video quality and other operational standards. At 2614 the camera head and any associated accessories may be packaged in a biohazard bag or sanitation bag. Such bags may provide the ability to sanitize the camera head while inside the bag. The sanitation process may include or be accomplished using Ethylene-Oxide (EO) gas, or other fluid process corresponding to the properties of said bag or packaging. At 2616 the packaged camera head and any associated accessories may then be sanitized. At 2618 the camera head and any associated accessories may be further packaged such as in a tray and shipped to an end user.

Figure 27:
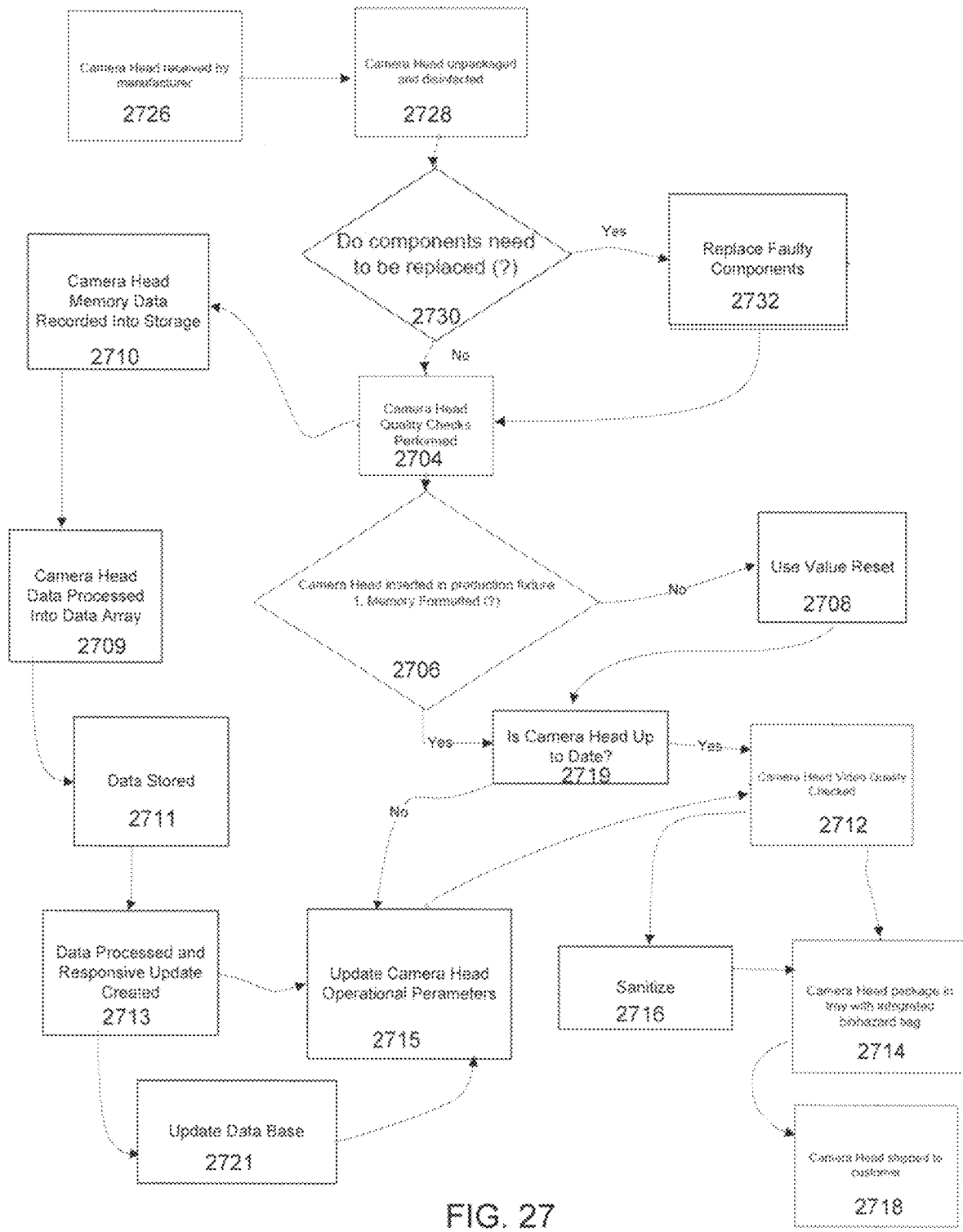
FIG. 27 illustrates an embodiment of a system for the reprocessing of a surgical imaging device and providing updates for said imaging device.

FIG. 27 illustrates an embodiment of a system for the reprocessing of a surgical camera head or imaging device and providing updates for said camera head or imaging device. Reprocessing may represent the reclaiming or recycling of a used surgical camera head and any associated accessories or components of said surgical camera head. At 2726 the manufacturer or processing facility may receive the used camera head and any associated accessories, and at 2728 the camera head and any associated accessories may be unpackaged and disinfected for further processing. At 2730 the camera head and any associated accessories may be inspected to determined whether components need to be replaced. If it is determined that some components of the camera head and any associated accessories need to be replaced, at 2732 the faulty components will be replaced. After the faulty components have been replace at 2732, the camera head and any associated accessories may be checked for quality and functionality at 2704, and then further processed in accordance to the illustrated system. At 2704 the assembled camera and any accessories are checked for proper operation, quality and functionality. At 2706 the camera head and any associated accessories may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 2708. If the production control unit determines that data and control values in the memory indicate that the camera is operational or has not been used, the data in the memory will be recorded and stored in a data base while a value or values allowing it to function will be written in to the memory of the camera head at 2710. A processor within a computer may be employed to read and record into storage data from said camera head at 2709 and the data may be stored for later use at 2711.

At 2719 it may be determined whether the operation of the camera head is up to date. At 2713 updates may be created to improve or modify the camera head. The update may be derived from camera head data stored at 2711 and may be responsive to said camera head data. At 2715 the camera head may be updated. At 2721 updates may be stored in an update data base such that when a camera head is found to be out of date the needed updates may be selected from the update data base and applied to the camera head. Such updates may be written to the memory of the camera head and may be done manually, automatically, at the point of operation or over a network connection.

At 2712 the camera head and any associated accessories may be tested for video quality and other operational standards. At 2714 the camera head and any associated accessories may be packaged in a biohazard bag or sanitation bag. Such bags may provide the ability to sanitize the camera head while inside the bag. The sanitation process may include or be accomplished using Ethylene-Oxide (EO) gas, or other fluid process corresponding to the properties of said bag or packaging. At 2716 the packaged camera head and any associated accessories may then be sanitized. At 2718 the camera head and any associated accessories may be further packaged such as in a tray and shipped to an end user.

Figure 28:
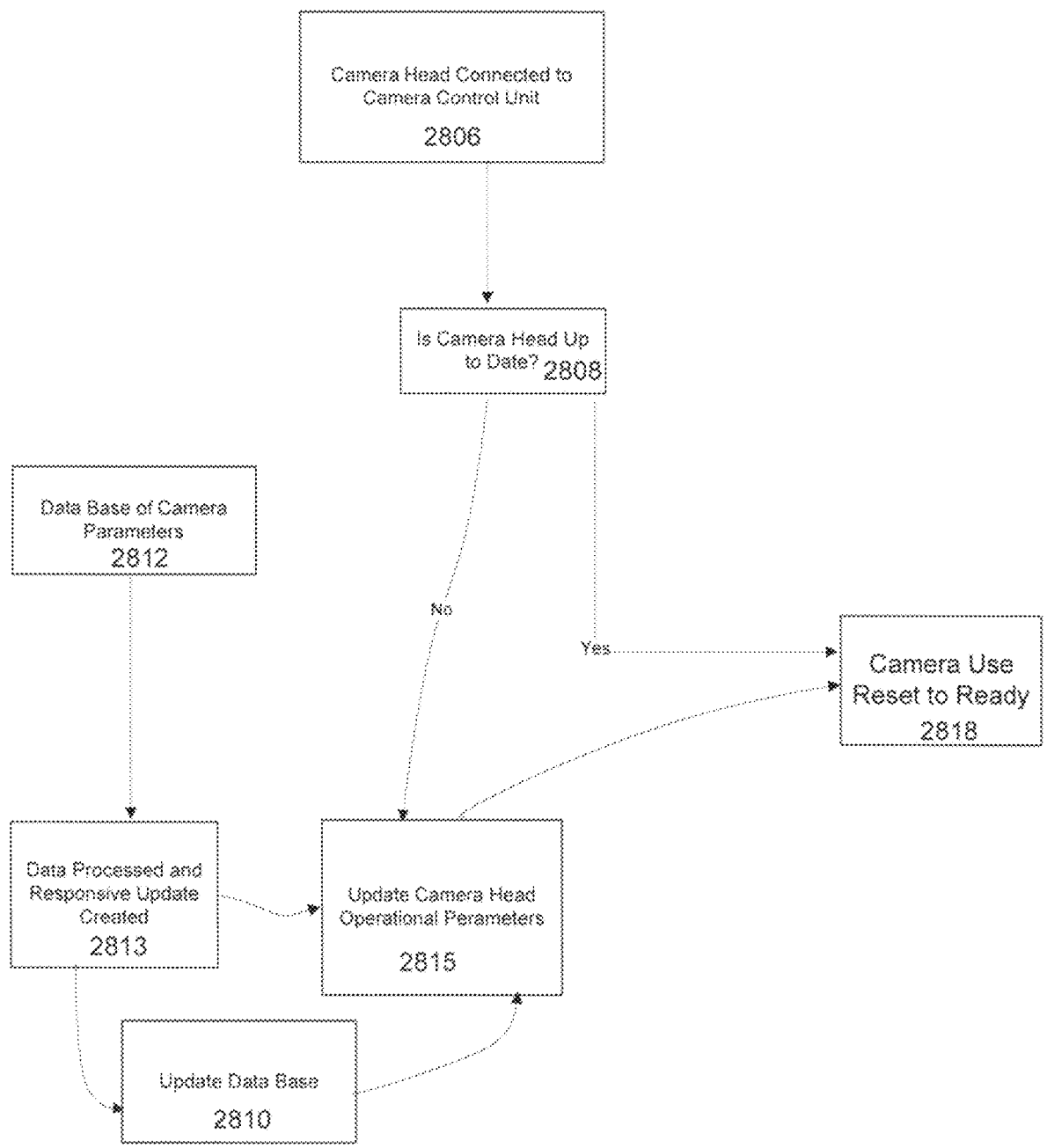
FIG. 28 illustrates an embodiment of a system for updating a surgical imaging device.

FIG. 28 illustrates an embodiment of a system for updating a surgical camera head or imaging device. At 2806 the camera head and any associated accessories may be inserted into a camera control unit. The camera control unit may check the condition of the memory within the camera head to determine whether the camera head has been updated at 2808. If the camera control unit determines that the camera head has been updated the memory will be written with a value or values allowing it function at 2808. If the production control unit determines that data and control values in the memory indicate that the camera has not been updated at 2808, the needed updates will be retrieved from an update data base at 2810. A processor within a computer may be employed to read camera parameters at 2812 and retrieve responsive updates at 2814. The update may be derived from camera head data stored and may be responsive to said camera head data. At 2815 the camera head may be updated. Updates may be stored in an update data base such that when a camera head is found to be out of date the needed updates may be selected from the update data base and applied to the camera head. Such updates may be written to the memory of the camera head and may be done manually, automatically, at the point of operation or over a network connection. At 2818 a value or values may be written to the camera head memory making the camera head ready for use.

Figure 29:
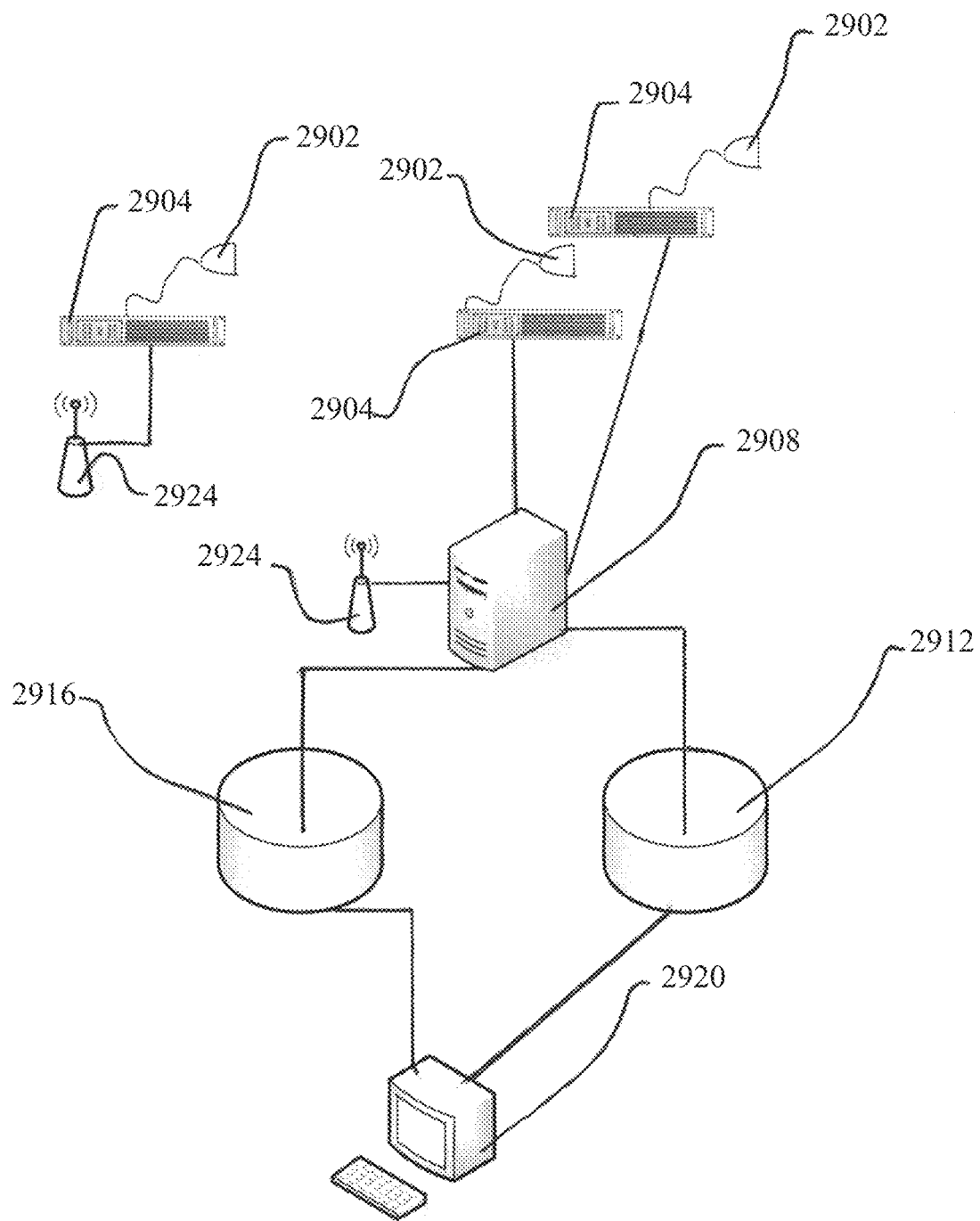
FIG. 29 illustrates an embodiment of a system for providing updates to a surgical imaging device.

FIG. 29 illustrates an embodiment of a system for providing updates to a surgical camera head or imaging device. The camera head 2902 may be configured to operate in conjunction with a camera control unit 2904. The system may be configured to operate as a network consistent with current network art and technologies as well as future network art and technologies that may be used in the future. The system may comprise a server 2908 configured with communication means for operating over a network and communicating with camera control units 2904. The system may comprise a data base or a plurality of data bases for storing data such as update data and camera head parameters. The system may comprise an update data base 2912 and a camera head data base 2916. The system comprise a computer terminal 2920 providing access to the network. The system may use a LAN based method of communication between networked components and/or it may use wireless communications provide by wireless means 2924.

Figure 30:
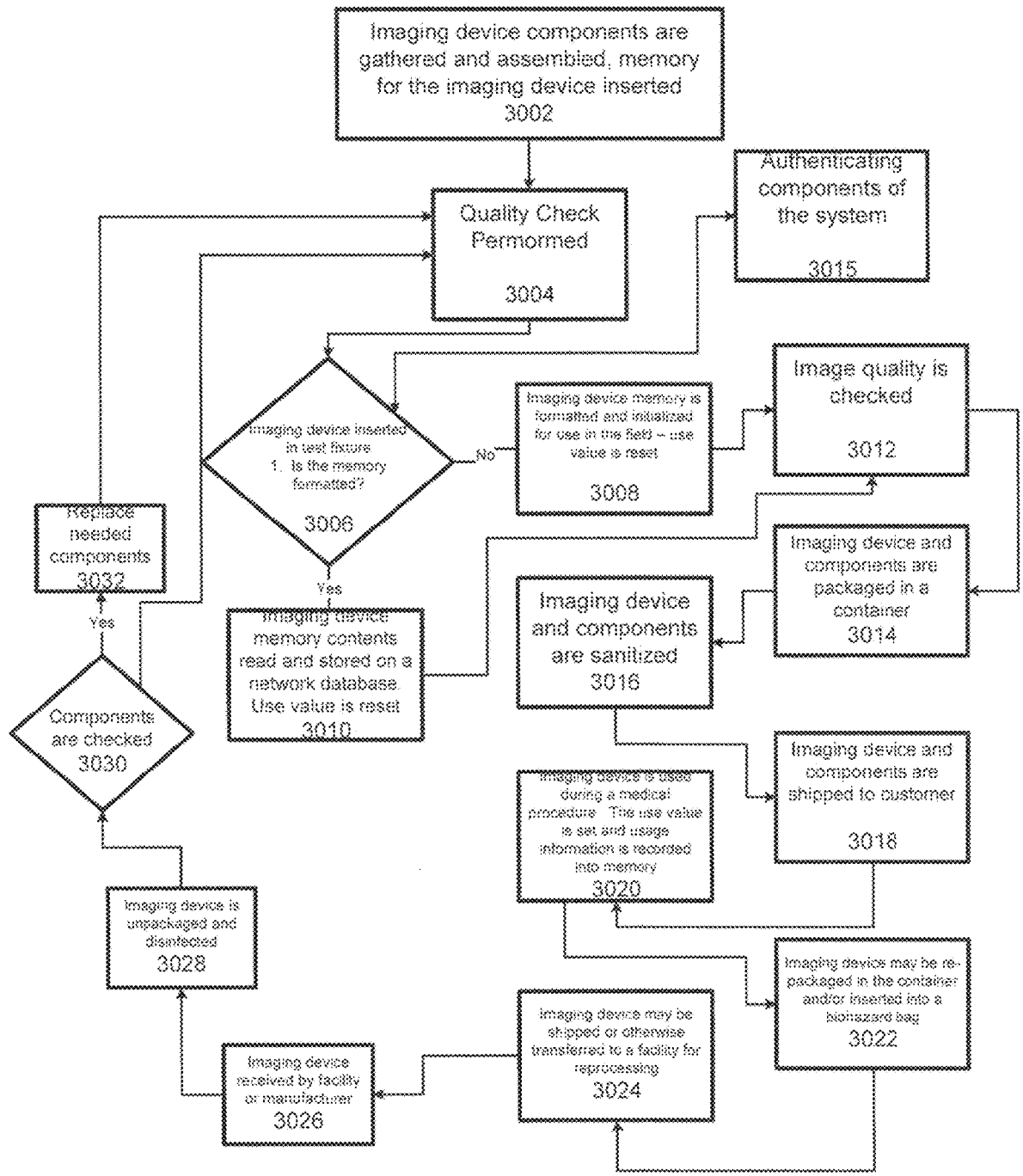
FIG. 30 illustrates an embodiment of a system for the manufacture and reprocessing of a surgical imaging device in accordance with the teachings and principles of the disclosure.

FIG. 30 illustrates an embodiment of a system and method for the manufacture and reprocessing of a surgical camera head or imaging device. Reprocessing may represent the reclaiming or recycling of a used surgical camera head and any associated accessories or components of said surgical camera head and may be referred to individually or collectively herein as an imaging device or a camera head. At 3002 the camera head components are assembled into a working unit having memory. At 3004 the assembled camera head is checked for proper operation and quality to ensure the assembled camera head passes a pre-determined minimum standard. At 3006 the camera head may be inserted into a production control unit or production fixture. The production control unit may check the condition of the memory within the camera head to determine whether the memory has been formatted to a predetermined operational condition. If the production control unit determines that data and control values in the memory indicate the camera has been used the memory will be written with a value or values allowing it function at 3008. If the production control unit determines that data and control values in the memory indicate that the camera is operational or has not been used, the data in the memory will be recorded and stored in a data base while a value or values allowing it to function will be written in to the memory of the camera head at 3010.

It will be appreciated that the imaging device or other component may be electronically connected to the test fixture or another component at 3006. When components are electronically connected, the components may authenticate each other via a communication between the components at 3015. For example, the authentication may be between the test fixture and the imaging device, but any components or devices may be authenticated with the same procedure or manner, and the authentication may be done by complying with certain encryption security protocols. In an embodiment, the security protocols originate in the imaging device. In an embodiment, the security protocols originate in the test fixture. It will be appreciated that the test fixture may be controlled with a separate computer. The separate computer may encrypt communication between the test fixture and the separate computer.

It should be appreciated that the communication between the components of an embodiment may be encrypted for security and access control. By encrypting the communication data streams, a user or provider can protect against tampering and thereby control the quality of the components. It is within the scope of this disclosure to contemplate any manner of encryption and security currently available, in addition to those methods that will be developed in the future.

In an embodiment the communication components may have fixed keys that allow for the transmitting component to insert obfuscating data into the data stream that will need to be removed by the receiving component of the system. Without the key the data would not be readily useable. In an embodiment an imaging device, such as a camera head, may perform the insertion of the obfuscating data in the data stream. In an embodiment a control unit may perform the insertion of the obfuscating data, and typically both components will perform this roll. In use, both the output data and the instructions between components can be encrypted. The keys may be embedded in hardware components, may be firm ware, or may be software based.

An embodiment may include the use of public and private keys wherein either the control unit or the imaging device is the originator of the respective keys. In an embodiment the public keys may be matched between the components from the outset of operation, or the keys may be derived on the fly having correspondence values between the components. An embodiment may comprise a method wherein the encryption originates in the imaging device. An embodiment may comprise a method wherein the encryption originates in a control unit. An embodiment may comprise additional components connected to a control unit or imaging device such as a separate computer, and in such an embodiment all or some of the communication between the components may be encrypted.

An embodiment may comprise levels of encryption wherein the keys them selves are encrypted in one level and the data is encrypted in a second level. Additionally, it should be noted that the encryption method may be updated and changed globally. An update may occur at the time of reprocessing or the update may occur at the time of use. Such updates may be performed locally or may be performed over a network.

In the event of tampering an embodiment may cause the components of the system to lock out further use or access. In another embodiment, the components may be configured to self destruct in the event of tampering.

At 3012 the camera head may be tested for video quality and other operational standards. The inspection and testing of video quality and other operational standards may include a visual inspection of the video/image quality against a known, acceptable image standard. It will be appreciated that this procedure may be automated, such that if the image does not meet a certain pre-determined quality standard the on screen check will return with a "use or no-use" or "go or no-go" on screen reply or signal.

At 3014 the camera may be packaged in a container, such as a tray, pouch, bag or the like, which may be sterilized along with the components within the container. Such containers may provide the ability to sanitize the camera head while inside the container. This package or container of components may then be sanitized or sterilized as noted at 3016. It will be appreciated that in an embodiment, the components included in the container, such as a tray, pouch, bag or the like, may also include a biohazard bag or sanitation bag. The biohazard bag may be used after an imaging device and related components have been used or otherwise contaminated to return the used or contaminated imaging device, along with any components, to a reprocessing center or agent for disinfection and further reprocessing treatment.

At 3016 the packaged camera head may then be sanitized or sterilized. It will be appreciated that there are many methods for sanitizing, sterilizing or otherwise eliminating (killing) transmissible agents, such as fungi, bacteria, viruses, bacterial spores, etc. from surgical tools and equipment. Such methods are within the scope of the disclosure. Sterilization may be accomplished using one or more of the following heat, chemicals, irradiation, and high pressure systems. Examples of the sanitization or sterilization methods may include ethylene oxide, gamma radiation, chemicals and autoclave systems.

At 3018, the imaging device, i.e., camera head and any accompanying components, may be further packaged and shipped to an end user. The camera head may then be used for a surgical procedure where during the procedure a camera control unit writes to the memory in the camera head where a use value or use bit may be set at 3020. After use or contamination, the camera head may be placed in a return shipping container suitable for biohazard shipping at 3022 and shipped to a processing facility or manufacturer at 3024. At 3026 the processing facility or manufacturer may receive the used or otherwise contaminated camera head and, at 3028, the camera head may be unpackaged and disinfected for further processing. It will be appreciated that the disinfection process is for worker safety where handlers of the used or otherwise contaminated camera head wear protective clothing, such as gloves and gowns. The disinfection process may include chemical treatment of the used or otherwise contaminated imaging device or camera head to meet low-level or other appropriate governmental standards for disinfection. Various chemicals may be used for the initial disinfection process and may include alcohols, aldehydes, and oxidizing agents. It will be appreciated that other disinfection processes may be used to initially treat the used or otherwise contaminated camera head without departing from the scope of the disclosure.

At 3030 the camera head may be inspected to determined whether components need to be replaced. If it is determined that some components of the camera head need to be replaced, then at 3032 the faulty components will be replaced. For example, components that may be replaced include cables, imaging device connectors, and buttons. However, it should be noted that during this inspection all components may be replaced on an as needed basis. After the faulty components have been replaced at 3032, the camera head may be checked for quality and functionality at 3004, and then further processed in accordance to the illustrated system.

Figure 31:
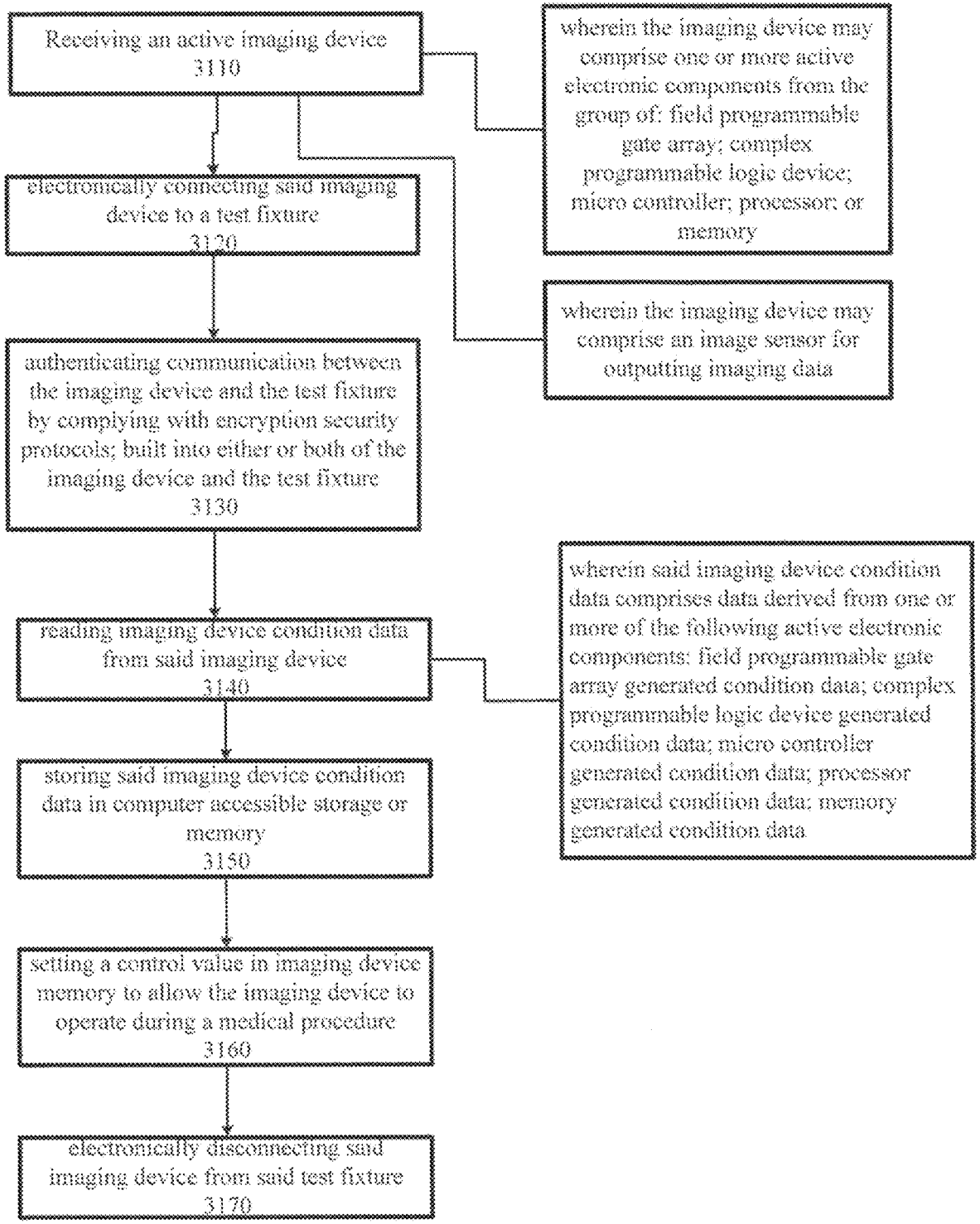

Referring to FIGS. 31-33 illustrate embodiments of a method and system for processing medical electronic imaging devices in accordance with the teachings and principles of the disclosure. In FIG. 31, a method for processing an active imaging device intended for use during medical procedure is illustrated. In FIG. 32, a method of authenticating an active imaging device intended for use during medical procedure is illustrated. In FIG. 33, a method of re-setting a control value in an imaging device, which may be a passive imaging device, is illustrated.

It will be appreciated that the above system or method for the manufacture and reprocessing of a surgical camera head or imaging device may include details relating to the camera head itself or the various processes within each step noted, which may be utilized by any of the embodiments disclosed herein and such details are incorporated into each of the embodiments.

In the foregoing Detailed Description, various features of the disclosure are grouped together in a single embodiment for the purpose of streamlining the disclosure. This method of disclosure is not to be interpreted as reflecting an intention that the claimed disclosure requires more features than are expressly recited in each claim. Rather, as the disclosure reflects, inventive aspects lie in less than all features of a single foregoing disclosed embodiment. Thus, the following claims are hereby incorporated into this Detailed Description by this reference, with each claim standing on its own as a separate embodiment of the disclosure.

It is to be understood that the above-described arrangements are only illustrative of the application of the principles of the disclosure. Numerous modifications and alternative arrangements may be devised by those skilled in the art without departing from the spirit and scope of the disclosure and the disclosure is intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for processing medical electronic imaging devices intended for use during medical procedures, the method comprising:
   receiving an active imaging device that has been previously powered on and then powered off for an elapsed amount of off and that comprises:
   one or more active electronic components from the group of: field programmable gate array; complex programmable logic device; micro controller; processor; or memory;
   wherein, when the elapsed amount of off time since the active imaging device was previously powered off is greater than or equal to a predetermined amount of time,
   wherein the predetermined amount of time equates to a time indicating the imaging device has been tampered with or that is approximately equivalent to a sterilization cycle,
   the active imaging device is disabled, thereby preventing further use of the active imaging device;
   electronically connecting said active imaging device to a test fixture to power on the active imaging device; and
   resetting the off time of the active imaging device to allow the active imaging device to operate during a medical procedure based on an authenticated communication with the test fixture and sterilization of the active imaging device.

2. The method of claim 1, wherein the method further comprises packaging the imaging device for conveying to a user.

3. The method of claim 1, wherein the method further comprises authenticating communication between the imaging device and the test fixture by complying with encryption security protocols.

4. The method of claim 1, wherein the method further comprises controlling said test fixture with a separate computer.

5. The method of claim 1, wherein the method further comprises reading imaging device condition data from said imaging device;
   wherein said imaging device condition data comprises data derived from one or more of the following active electronic components:
   field programmable gate array generated condition data; complex programmable logic device generated condition data; micro controller generated condition data; processor generated condition data; and memory generated condition data.

6. The method of claim 1, wherein the method further comprises electronically disconnecting said imaging device from said test fixture.

7. The method of claim 3, wherein said security protocols originate in said imaging device.

8. The method of claim 3, wherein said security protocols originate in said test fixture.

9. The method of claim 4, wherein the method further comprises encrypting communication between said test fixture and said separate computer.

10. The method of claim 5, wherein the method further comprises storing said imaging device data in computer accessible storage or memory.

11. A method for updating medical electronic imaging devices intended for use during medical procedures, the method comprising:
   receiving an active imaging device that has been previously powered on and then powered off for an elapsed amount of off time and that comprises:
   one or more active electronic components from the group of: field programmable gate array; complex programmable logic device; micro controller; processor; or memory;
   wherein, when the elapsed amount of off time since the active imaging device was previously powered off is greater than or equal to a predetermined amount of time,
   wherein the predetermined amount of time equates to a time indicating the imaging device has been tampered with or that is approximately equivalent to a sterilization cycle,
   the active imaging device is disabled, thereby preventing further use of the active imaging device;
   providing updated programming for one or more of said active electronic components;
   electronically connecting said active imaging device to a test fixture to power on the active imaging device; and
   resetting the off time of the active imaging device to allow the active imaging device to operate during a medical procedure based on an authenticated communication with the test fixture and sterilization of the active imaging device.

12. The method of claim 11, wherein the method further comprises authenticating communication between the imaging device and the test fixture by complying with encryption security protocols.

13. The method of claim 11, wherein the method further comprises controlling said test fixture with a separate computer.

14. The method of claim 11, wherein the method further comprises reading imaging device condition data from said imaging device;
   wherein said imaging device condition data comprises data derived from one or more of the following active electronic components: field programmable gate array generated condition data; complex programmable logic device generated condition data; micro controller generated condition data; processor generated condition data; memory generated condition data.

15. The method of claim 11, wherein the method further comprises transmitting and receiving said updated programming over a network.

16. The method of claim 11, wherein the method further comprises connecting said imaging device to a control unit for use during a surgical procedure and receiving said updated programming from said control unit.

17. The method of claim 12, wherein said security protocols originate in said imaging device.

18. The method of claim 12, wherein said security protocols originate in said test fixture.

19. The method of claim 13, wherein the method further comprises encrypting communication between said test fixture and said separate computer.

20. The method of claim 14, wherein the method further comprises storing said imaging device data in computer accessible storage or memory.

21. The method of claim 16, wherein the method further comprises providing said updated programming to said control unit over a network.

22. The method of claim 16, wherein the method further comprises authenticating communication between said control unit and said imaging device by complying with encryption security protocols.

23. The method of claim 16, wherein the method further comprises controlling said control unit with a separate computer.

24. The method of claim 16, wherein the method further comprises reading imaging device condition data from said imaging device;
   wherein said imaging device condition data comprises data derived from one or more of the following active electronic components:
   field programmable gate array generated condition data; complex programmable logic device generated condition data; micro controller generated condition data; processor generated condition data; memory generated condition data.

25. The method of claim 22, wherein said security protocols originate in said imaging device.

26. The method of claim 22, wherein said security protocols originate in said control unit.

27. The method of claim 23, wherein the method further comprises encrypting communication between said control unit and said separate computer.

28. The method of claim 24, wherein the method further comprises storing said imaging device data in computer accessible storage or memory.

29. The method of claim 24, wherein the method further comprises transmitting and receiving said imaging device data over a network.

30. The method of claim 29, wherein the method further comprises tracking said imaging device by said imaging device data in order to control imaging devices in circulation.

* * * * *